United States Patent [19]

Henrie, II et al.

[11] Patent Number: 5,532,370
[45] Date of Patent: Jul. 2, 1996

[54] 2,4-DIAMINO-5,6-DISUBSTITUTED- AND 5,6,7-TRISUBSTITUTED 5-DEAZAPTERIDINES AS INSECTICIDES

[75] Inventors: Robert N. Henrie, II, East Windsor; Clinton J. Peake, Trenton; Thomas G. Cullen, Milltown; Munirathnam K. Chaguturu, Lawrenceville, all of N.J.; Partha S. Ray, Memphis, Tenn.; Brian D. Bennett, Lake Hopatcong, N.J.

[73] Assignee: FMC Corporation, Philadelphia, Pa.

[21] Appl. No.: 425,524

[22] Filed: Apr. 20, 1995

Related U.S. Application Data

[62] Division of Ser. No. 249,586, May 26, 1994.

[51] Int. Cl.⁶ .................................................. C07D 487/04
[52] U.S. Cl. ................................. 544/279; 544/117
[58] Field of Search ......................... 544/279, 117

[56] References Cited

U.S. PATENT DOCUMENTS 5,286,726  2/1994  Bey et al. .................... 514/249
5,374,726  10/1994  DeGraw et al. ............... 544/260

*Primary Examiner*—Richard L. Raymond
*Attorney, Agent, or Firm*—Stanford M. Back; Robert M. Kennedy

[57] ABSTRACT

An insecticidal composition comprising, in admixture with an agriculturally acceptable carrier, an insecticidally effective amount of a 5-deazapteridine compound of the formula:

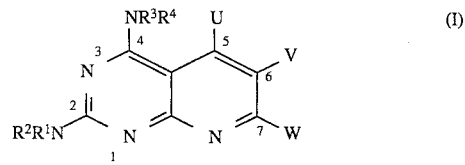

wherein $R^1$, $R^2$, $R^3$, $R^4$, U, V, and W are as defined herein; agriculturally acceptable salts thereof; methods for using the same; and certain novel 5-deazapteridines per se.

2 Claims, No Drawings

2,4-DIAMINO-5,6-DISUBSTITUTED- AND 5,6,7-TRISUBSTITUTED 5-DEAZAPTERIDINES AS INSECTICIDES

This application is a division of application Ser. No. 08/249,586, filed May 26, 1994, pending.

BACKGROUND OF THE INVENTION

This invention relates to substituted-5-deazapteridine compounds and compositions containing the same which are useful for controlling insects in agricultural crops. More particularly, this invention relates to certain 2,4-diamino-5,6-disubstituted-and 5,6,7-trisubstituted-5-deazapteridine compounds, and compositions, and their use as insecticides against a variety of insects, including larvae, such as the tobacco budworm. Certain of the 5-deazapteridine compounds employed herein, and their preparation, have been described in the literature for use in a variety of fields, but not as insecticides.

SUMMARY OF THE INVENTION

In accordance with the present invention it has been found that certain defined substituted-pteridines, more particularly 2,4-diamino-5,6-disubstituted-and 5,6,7-trisubstituted-5-deazapteridines (hereinafter "5-deazapteridines"), and agriculturally acceptable salts thereof, when present in insecticidally effective amounts, and with a suitable agricultural carrier, are useful as active ingredients in the insecticidal compositions and methods of this invention. These pteridines may be represented by the following formula:

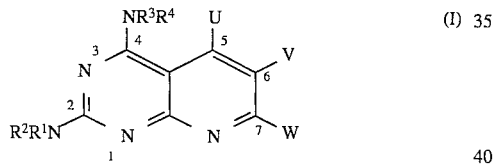

wherein $R^1$ is hydrogen, lower alkyl or arylalkyl (e.g., phenylmethyl);

$R^3$ is hydrogen, lower alkyl or arylalkyl (e.g., phenylmethyl);

$R^2$ and $R^4$ are independently hydrogen, lower alkyl, arylalkyl (e.g., phenylmethyl), or

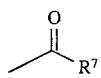

wherein $R^7$ is straight or branched chain alkyl [e.g., —$CH_3$, —$CH(CH_3)_2$, —$C(CH_3)_3$, —$C_5H_{11}$, —$C_8H_{17}$, $C_{11}H_{23}$], lower haloalkyl (e.g., —$CF_2CF_3$), lower alkynyl (e.g., —C≡$CCH_3$), straight or branched chain alkoxy [e.g., n—$OC_4H_9$, —$OC(CH_3)_3$], alkylsulfonylalkyl (e.g., —$CH_2SO_2CH_3$), aryl (e.g., phenyl), arylalkyloxy (e.g., phenylmethoxy), or ethers or polyethers of two to twelve carbon atoms in length containing one to four ether linkages (e.g.,—$CH_2OC_2H_5$, —$C_2H_4OC_2H_5$, —$C_2H_4OC_2H_4OC_2H_5$, —$CH_2OC_2H_4OC_2H_5$, —$CH_2OC_2H_4OC_2H_4OCH_3$); or $R^1$ and $R^2$ taken together, form the group —$R^8$-O-$R^8$, wherein $R^8$ is lower alkylene; or $R^1$ and $R^2$, taken together, and $R^3$ and $R^4$ taken together, each form the group

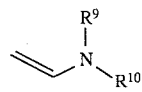

wherein $R^9$ and $R^{10}$ are independently straight or branched chain lower alkyl [e.g., —$CH_3$, —$CH(CH_3)_2$]; or $R^9$ and $R^{10}$ taken together with two to five methylene groups form an alkylene ring [e.g., —$(CH_2)_5$—];

W is hydrogen, halogen (e.g., Cl), lower alkyl (e.g., —$CH_3$,), or hydroxy;

U is hydrogen, halogen (e.g., Br, Cl, F, I), lower alkyl [e.g., —$CH_3$, —$CH(CH_3)_2$, —$C(CH_3)_3$], lower haloalkyl (e.g., —$CF_3$), lower alkoxy (e.g., —$OC_2H_5$), lower haloalkoxy (e.g., —$OCH_2CF_3$), lower dialkylamino [e.g., —$N(CH_3)_2$], aryl (e.g., phenyl), arylalkyl [e.g., 2-(naphth-2-yl)ethyl], substituted arylthio [e.g., 3,4-dichlorophenylthio], substituted arylsulfinyl [e.g., 3,4-dichlorophenylsulfinyl], or substituted arylalkylthio [e.g., 3,4-dichlorophenylmethylthio]; wherein the chloro substituent may be replaced by other halogens; and V is hydrogen, lower haloalkyl (e.g., —$CF_3$), thienyl, aryl (e.g., phenyl, naphthyl) or substituted aryl, arylalkyl (e.g., phenyl-methyl) or substituted arylalkyl, aryloxy (e.g., phenoxy) or substituted aryloxy (e.g., 4-chlorophenoxy), arylthio (e.g., 2-naphthylthio) or substituted arylthio, arylsulfinyl (e.g., 2-naphthylsulfinyl) or substituted arylsulfinyl, arylsufonyl (e.g., 2-naphthylsulfonyl) or substituted arylsulfonyl, substituted arylalkylamino, (aryl)(halo)alkenyl or substituted (aryl)(halo) alkenyl, aroyl (e.g., benzoyl) or substituted aroyl, substituted arylalkylcarbonylamino, substituted (aryl)(alkyl)aminoalkyl, or a benzo-fused oxygen-containing heterocycle of the formula:

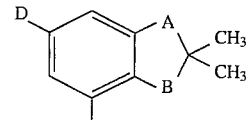

wherein

A and B may independently be selected from methylene, carbonyl, and oxygen, and wherein at least one of A and B is always oxygen, as for example

| A | B |
|---|---|
| —$CH_2$— | O |
| O | —$CH_2$— |
| —C=O | O |
| O | —C=O |
| O | O; | and wherein D is hydrogen, halogen (e.g., Cl, Br), lower alkyl (e.g., —$CH_3$), or lower haloalkyl (e.g., —$CF_3$); to form, for example, the heterocycles 2,3-dihydro-2,2-dimethylbenzofuran-4-yl, 2,3-dihydro-2,2-dimethylbenzofuran-7-yl, 6-halo-2,3-dihydro-2,2-dimethyl-benzofuran-4-yl, 5-halo-2,3-dihydro-2,2-dimethylbenzofuran-7-yl, 2,3-dihydro-2,2-dimethyl-3-benzofuranon-4-yl, or 2,2-dimethyl-5-halobenzodioxol-7-yl;

and agriculturally acceptable salts thereof.

Agriculturally acceptable salts of the 5-deazapteridines include, but are not limited to, for example, the salts of hydrochloric acid, ethanesulfonic acid, gluconic acid, and pamoic acid.

Where the V moiety is defined as being substituted, as described above, e.g., substituted aryl or the like, these substituted groups include the following:

(a) substituted aryl (e.g., phenyl, naphthyl), substituted arylalkyl, substituted arylthio, substituted arylsulfinyl, substituted arylsulfonyl, and substituted arylalkylamino, wherein the substituents are selected from one or more of alkyl, halogen (e.g., Cl, Br, F), lower alkoxy [e.g., —$OCH_3$, —$OC_3H_7$, $OCH(CH_3)_2$], lower haloalkyl (e.g., —$CF_3$), lower haloalkoxy (e.g., —$OCF_3$), lower alkoxyalkyl (e.g., —$CH_2OCH_3$), lower alkoxycarbonyl (e.g., —$CO_2CH_3$), cyano, lower alkylthio (e.g., —$SC_2H_5$, —$SC_4H_9$), and lower alkylsulfonyl [e.g., —$S(O)_2C_2H_5$, —$S(O)_2C_4H_9$];

(b) substituted aryl selected from the formulas:

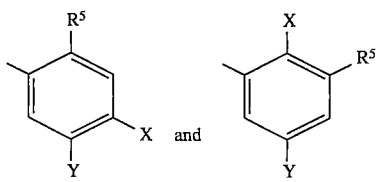

where X and Y are independently hydrogen, halogen (e.g., Cl, F), lower alkyl (e.g., —$CH_3$), or lower haloalkyl (e.g., —$CF_3$); and $R^5$ is phenyl, or phenyl substituted with one or more of halogen (e.g., Cl, F) or haloalkyl (e.g., —$CF_3$);

(c) substituted aryl selected from the formulas:

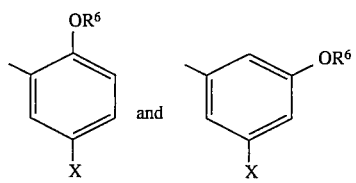

where X is hydrogen, halogen (e.g., Cl, F), lower alkyl (e.g., —$CH_3$), lower haloalkyl (e.g., —$CF_3$), or lower haloalkoxy (e.g., —$OCF_3$); and $R^6$ is methyl, 1-methylethyl, phenyl, phenyl substituted with one or more of halogen (e.g., Cl, F), or halogen-substituted phenyl lower alkyl [e.g., 4-chlorophenylmethyl, or 4-(4-chlorophenyl)butyl];

(d) substituted (aryl)(halo)alkenyl of the formula:

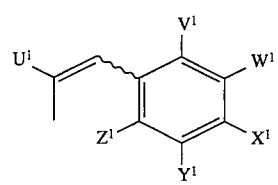

where $U^1$, $V^1$, $W^1$, $X^1$, $Y^1$, and $Z^1$ are independently hydrogen, halogen (e.g., Cl), or lower haloalkyl (e.g., —$CF_3$);

(e) substituted aroyl of the formula:

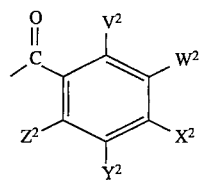

where $V^2$, $W^2$, $X^2$, $Y^2$, and $Z^2$ are independently hydrogen, halogen (e.g., Cl, F), lower haloalkyl (e.g., —$CF_3$), lower alkoxycarbonyl (e.g., —$CO_2CH_3$), 4-chlorophenyl, or 4-fluorophenyl;

(f) substituted arylalkylcarbonylamino of the formula:

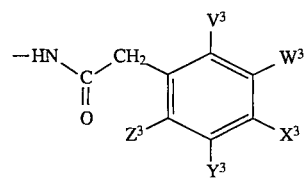

where $V^3$, $W^3$, $X^3$, $Y^3$, and $Z^3$ are independently hydrogen or halogen (e.g., Cl);

(g) substituted (aryl)(alkyl)aminoalkyl of the formula:

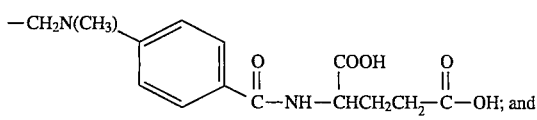

(h) substituted aryloxy of the formula:

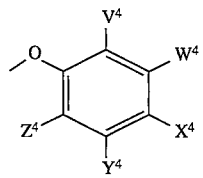

where $V^4$, $W^4$, $X^4$, $Y^4$, and $Z^4$ are independently hydrogen, halogen (e.g., Cl), or lower haloalkyl (e.g., —$CF_3$).

Of the 5-deazapteridine compounds of structure (I), among the more preferred ones for use in the compositions and methods of this invention are those wherein $R^1$, $R^2$, $R^3$, and $R^4$ are as defined above in structure (I), and wherein U is lower alkyl [e.g., —$CH_3$, —$CH(CH_3)_2$];

V is (i) a benzo-fused oxygen-containing heterocycle of the formula:

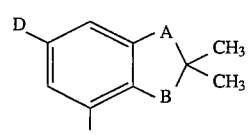

wherein

A and B may independently be selected from methylene, carbonyl, and oxygen, and wherein at least one of A and B is always oxygen, as for example

| A | B |
| --- | --- |
| —CH₂— | O |
| O | —CH₂— |
| —C=O | O |
| O | —C=O |
| O | O; | and wherein D is hydrogen, halogen (e.g., Cl, Br), lower alkyl (e.g., —CH₃), or lower haloalkyl (e.g., —CF₃); to form, for example, the heterocycles 2,3-dihydro-2,2-dimethyl-benzofuran-4-yl, 2,3-dihydro-2,2-dimethylbenzofuran-7-yl, 6-halo-2,3-dihydro-2,2-dimethylbenzofuran-4-yl, 5-halo-2,3-dihydro-2,2-dimethylbenzofuran-7-yl, 2,3-dihydro-2,2-dimethyl-3-benzofuranon-4-yl, or 2,2-dimethyl-5-halobenzodioxol-7-yl;

(ii) aryl (e.g., phenyl, naphthyl), or aryl substituted with one or more of halogen (e.g., Cl, Br, F), lower alkoxy [e.g., —OCH₃, —OCH(CH₃)₂, or lower haloalkyl (e.g., —CF₃);

(iii) substituted aryl of the formula:

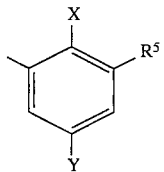

where X is hydrogen, Y is halogen (e.g., F), and R⁵ is phenyl substituted with one or more of halogen (e.g., Cl, F) or haloalkyl (e.g., —CF₃);

(iv) substituted aryl of the formula:

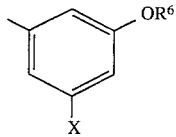

where X is halogen (e.g., Cl, F), lower alkyl (e.g., —CH₃), lower haloalkyl (e.g., —CF₃) or lower haloalkoxy (e.g., —OCF₃); and R⁶ is phenyl substituted with one or more of halogen (e.g., Cl, F) or lower alkyl (e.g., —CH₃);

(v) substituted (aryl)(halo)alkenyl of the formula:

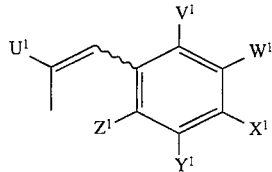

where U¹, V¹, W¹, X¹, Y¹, and Z¹ are independently hydrogen, halogen (e.g., Cl), or lower haloalkyl (e.g., —CF₃); or (vi) substituted aroyl of the formula:

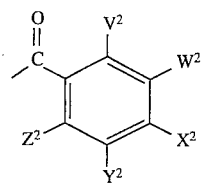

where V², W², X², Y², and Z² are independently hydrogen, halogen (e.g., Cl, F), or lower haloalkyl (e.g., —CF₃); and W is hydrogen.

In a further embodiment, this invention is also directed to certain novel substituted 5-deazapteridines per se and agriculturally acceptable salts thereof falling within the scope of structure (I) above. These compounds, as illustrated, for example, by Compounds 3–6, 13, 14, 16, 17, 20–26, 29–85, 94–115, 128–187, 190, 191, 193 and 194 of Table I below, include the following novel pteridines and 5-deazapteridines, which in the same manner as the above compounds, may be prepared by methods that are provided in the detailed synthesis description below and in the accompanying Examples 4–13, and 15–18:

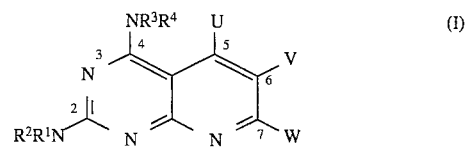

wherein

R¹ is hydrogen, lower alkyl, or arylalkyl (e.g., phenylmethyl);

R³ is hydrogen, lower alkyl, or arylalkyl (e.g., phenylmethyl);

R² and R⁴ are independently hydrogen, lower alkyl, arylalkyl (e.g., phenylmethyl), or

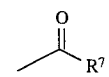

wherein R⁷ is straight or branched chain alkyl [e.g., —CH₃, —CH(CH₃)₂, —C(CH₃)₃, —C₅H₁₁, —C₈H₁₇, C₁₁H₂₃], cycloalkyl (e.g., cyclohexyl), lower haloalkyl (e.g., —CF₂CF₃), lower alkynyl (e.g., —C≡CCH₃), straight or branched chain alkoxy [e.g., n—OC₄H₉, —OC(CH₃)₃], alkylsulfonylalkyl (e.g., —CH₂SO₂CH₃), aryl (e.g., phenyl), arylalkyloxy (e.g., phenylmethoxy), or polyethers of two to twelve carbon atoms in length containing one to four ether linkages (e.g., —CH₂OC₂H₅, —C₂H₄OC₂H₅, —C₂H₄OC₂H₄OC₂H₅, —CH₂OC₂H₄OC₂H₅, —CH₂OC₂H₄—OC₂H₄OCH₃); or R¹ and R² taken together, and R³ and R⁴ taken together, each form the group —R⁸—O—R⁸, wherein R⁸ is lower alkylene; or form the group

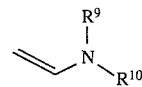

wherein R⁹ and R¹⁰ are independently straight or branched chain lower alkyl [e.g., —CH₃, —CH(CH₃)₂], or $R^9$ and $R^{10}$ taken together with two to five methylene groups form an alkylene ring [e.g., —$(CH_2)_5$—];

W is hydrogen, halogen (e.g., Cl), lower alkyl (e.g., —$CH_3$,), or hydroxy;

U is hydrogen, halogen (e.g., Br, Cl, F, I), lower haloalkyl (e.g., —$CF_3$), lower alkoxy (e.g., —$OC_2H_5$), lower haloalkoxy (e.g., —$OCH_2CF_3$), lower dialkylamino [e.g., —$N(CH_3)_2$], arylalkyl [e.g., 2-(naphth-2-yl)ethyl], substituted arylthio [e.g., 3,4-dichlorophenylthio], substituted arylsulfinyl [e.g., 3,4-dichlorophenylsulfinyl], or substituted arylalkylthio [e.g., 3,4-dichlorophenylmethylthio]; wherein the chloro substituent may be replaced by other halogens; and V is lower haloalkyl (e.g., —$CF_3$), thienyl, substituted aryl, arylsufinyl (e.g., 2-naphthylsulfinyl) or substituted arylsulfinyl, arylsulfonyl (e.g., 2-naphthylsulfonyl) or substituted arylsulfonyl, (aryl)(halo)alkenyl or substituted (aryl)(halo) alkenyl, aroyl (e.g., benzoyl) or substituted aroyl, or a benzo-fused oxygen-containing heterocycle of the formula:

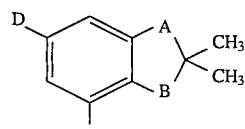

A and B may independently be selected from methylene, carbonyl, and oxygen, and wherein at least one of A and B is always oxygen, as for example

| A | B |
|---|---|
| —$CH_2$— | O |
| O | —$CH_2$— |
| —C=O | O |
| O | —C=O |
| O | O; and | wherein D is hydrogen, halogen (e.g., Cl, Br), lower alkyl (e.g., —$CH_3$), or lower haloalkyl (e.g., —$CF_3$); to form, for example, the heterocycle 2,3-dihydro-2,2-dimethylbenzofuran-4-yl, 2,3-dihydro-2,2-dimethylbenzofuran-7-yl, 6-halo-2,3-dihydro-2,2-dimethylbenzofuran-4-yl, 5-halo-2,3-dihydro-2,2-dimethylbenzofuran-7-yl, 2,3-dihydro-2,2-dimethyl-3-benzofuranon-4-yl, or 2,2-dimethyl-5-halobenzodioxol-7-yl, wherein the substituent groups of V are as defined above.

Of these novel compounds, particularly preferred ones include those wherein the 5-deazapteridines are of the general structure (I) above, and wherein $R^1$, $R^2$, $R^3$, $R^4$ and W are hydrogen;

U is lower alkyl [e.g., —$CH_3$, —$CH(CH_3)_2$]; and

V is substituted aryl, aroyl or substituted aroyl, (aryl)(halo)alkenyl or substituted (aryl)(halo)alkenyl, or a benzo-fused oxygen-containing heterocycle, as defined above, i.e., of the formula:

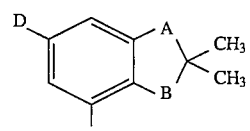

wherein, A and B are as defined above, i.e., for example

| A | B |
|---|---|
| —$CH_2$— | O |
| O | —$CH_2$— |
| —C=O | O |
| O | —C=O |
| O | O; and | wherein D is hydrogen, halogen (e.g., Cl, Br), lower alkyl (e.g., —$CH_3$), or lower haloalkyl (e.g., —$CF_3$); to form, for example, the heterocycle 2,3-dihydro-2,2-dimethylbenzofuran-4-yl, 2,3-dihydro-2,2-dimethylbenzofuran-7-yl, 6-halo-2,3-dihydro-2,2-dimethylbenzofuran-4-yl, 5-halo-2,3-dihydro-2,2-dimethylbenzofuran-7-yl, 2,3-dihydro-2,2-dimethyl-3-benzofuranon-4-yl, or 2,2-dimethyl-5-halobenzodioxol-7-yl.

All of the above preferred compounds are preferred because of their high insecticidal activity. They may be used in controlling insects by applying to the locus where control is desired an insecticidal amount of these compounds admixed in a suitable agricultural carrier. When thus applied to insect-infected crops such as cotton, vegetables, fruits or other crops, these compounds are highly effective against an array of insects, particularly those shown in the tables below.

For the purposes of this invention, as regards the above substituent groups, the following definitions apply:

The term alkyl includes straight or branched chain alkyl of 1 to 14 carbon atoms, preferably lower straight or branched alkyl of 1 to 6 carbon atoms; while halogen includes chlorine, bromine, fluorine and iodine atoms. The term cycloalkyl includes rings of three to twelve carbon atoms, preferably rings of three to six carbon atoms. The terms haloalkyl and haloalkoxy include straight or branched chain alkyl of 1 to 14 carbon atoms, preferably lower straight or branched alkyl of 1 to 6 carbon atoms, wherein one or more hydrogen atoms have been replaced with halogen atoms, as, for example, trifluoromethyl and 2,2,2-trifluoroethoxy, respectively. The terms lower alkoxy and lower dialkylamino include those moieties having 1 to 6 carbon atoms, e.g., ethoxy and N,N-dimethylamino, respectively.

The terms aryl and substituted aryl include phenyl and naphthyl; preferably phenyl or substituted phenyl, while the terms aroyl and substituted aroyl include benzoyl and naphthoyl, preferably benzoyl or substituted benzoyl. The terms substituted aryl and aroyl include those groups substituted with one or more alkyl, halo, alkoxy, or haloalkyl groups, or the like, as defined above.

In addition, the term arylalkyl includes 2-(naphth-2-yl)ethyl; arylalkenyl includes 2-(naphth-2-yl)ethenyl; arylthio includes 3,4-dichlorophenylthio and naphth-2-ylthio; arylsulfinyl includes 3,4-dichlorophenylsulfinyl and naphth-2-ylsulfinyl; while arylsulfonyl includes 3,4-dichlorophenyisulfonyl and naphth-2-ylsulfonyl.

DETAILED DESCRIPTION OF THE INVENTION

Synthesis of the Compounds

The methods of preparation of the 2,4-diamino-5,6-disubstituted-5-deazapteridines employed as insecticides in accordance with this invention are generally known to those skilled in the art, including commercial preparations thereof, or may readily be prepared from these compounds by known methods.

In a method taught by C. A. Nichol et al (J. Med. Chem. 1980, 23, 327–329), ethyl 3-oxo-2-substituted-butanoate, for example, ethyl 3-oxo-2-phenylbutanoate or ethyl 3-oxo-2-(2,5-dimethoxyphenylmethy)butanoate, is cyclized with 2,4,6-triaminopyrimidine in diphenyl ether, affording the corresponding 2,4-diamino-7-hydroxy-5-methyl-6-substituted-5-deazapteridine. The 7-hydroxy intermediate is in turn chlorinated with thionyl chloride and N,N-dimethylformamide in chloroform, yielding the corresponding 2,4-diamino-7-chloro-5-methyl-6-substituted-5-deazapteridine. The 7-chloro intermediate is then hydrogenated in the presence of 5% palladium on charcoal in ethanol, affording the targeted 2,4-diamino-5-methyl-6-substituted-5-deazapteridine, for example, 2,4-diamino-5-methyl-6-(2,5-dimethoxyphenylmethy)-5-deazapteridine. Examples 1–3 provide a detailed description of the C. A. Nichol route to certain compounds of the present invention.

The method of C. A. Nichol is most useful in preparing desired compounds wherein the substituent in the 6-position of the 5-deazapteddine ring is optionally substituted phenylmethyl.

A number of the 2,4-diamino-7-hydroxy and 7-chloro-5-methyl-6-substituted-5-deazapteridine intermediates prepared by the method of C. A. Nichol are shown in Tables 1A and 1B.

A method to prepare certain 2,4-diamino-6-substituted-5-deazapteridines of the present invention commences with the preparation of 2-amino-3-cyano-4-methylpyridine, using methods taught by G. S. Ponticello et al (J. Org. Chem. 1978, 43, 2529–2535) and E. C. Taylor et al (J. Org. Chem. 1983, 48, 4852–4860). The so-prepared pyridine is then halogenated using either N-bromosuccinimide or N-iodosuccinimide in N,N-dimethylformamide, affording the corresponding 2-amino-3-cyano-4-methyl-5-halopyridine. The 5-halopyridine is then reacted with an appropriately substituted boronic acid in the presence of tetrakis(triphenylphosphine)palladium(0) in aqueous sodium carbonate and toluene, a method taught by W. J. Thompson and J. Gaudino (J. Org. Chem. 1984, 49, 5237–5243), yielding the corresponding 2-amino-3-cyano-4-methyl-5-substituted-pyridine, for example, 2-amino-3-cyano-4-methyl-5-[3,5-di(trifluoromethyl)phenyl]pyridine. The substituted boronic acid intermediates used in this step are either commercially available or are prepared by methods also taught by Thompson and Gaudino (cited above). The 2-amino-3-cyano-4-methyl-5-substituted-pyridine is then cyclized, using a method taught by Taylor et al (cited above), with guanidine in ethanol, yielding the corresponding targeted 2,4-diamino-5-methyl-6-substituted-5-deazapteridine, for example, 2,4-diamino-5-methyl-6-[3,5-di(trifluoromethyl)phenyl]-5-deazapteridine. Examples 4 and 5 provide a detailed description of how these reactions are conducted.

In a slight variation in the method to the 2,4-diamino-5,6-disubstituted-5-deazapteridines described above, using a method taught by A. Pidcock et al (J. Organometallic Chem. 1981, 215, 49–58), 4-bromo-2,3-dihydro-2,2-dimethyl-3-benzofuranone is reacted with hexamethylditin in the presence of tetrakis(triphenylphosphine)palladium(0)in toluene, yielding (2,3-dihydro-2,2-dimethyl-3-benzofuranon-4-yl)tin. The organometallic derivative is then reacted with 2-amino-3-cyano-5-iodo-4-methylpyridine, again in the presence of tetrakis(triphenylphosphine)palladium(0) in toluene, affording the corresponding 2-amino-3-cyano-5-(2,3-dihydro-2,2-dimethyl-3-benzofuranon-4-yl)-4-methylipyridine. This compound is then cyclized with guanidine in ethanol, as previously described, yielding the corresponding 2,4-diamino-5-methyl-6-(2,3-dihydro-2,2-dimethyl-3-benzofuranon-4-yl)-5-deazapteridine. Example 9 provides a detailed description of how this reaction is conducted.

In another variation in the method to the 2,4-diamino-5,6-disubstituted-5-deazapteridines described above, 2-amino-3-cyano-5-iodo-4-methylpyridine is reacted with trimethylsilylacetylene in the presence of copper(I) iodide and bis(triphenylphosphine)palladium(II) chloride under basic conditions in acetonitrile, affording 2-amino-3-cyano-4-methyl-5-(trimethylsilylethynyl)pyridine. The 5-(trimethylsilylethynyl)pyridine is in turn treated with potassium carbonate in methanol, yielding the corresponding 2-amino-3-cyano-4-methyl-5-ethynylpyridine. The 5-ethynylpyridine is then reacted with an appropriately substituted halide, for example, 4-trifluoromethyl-phenyl iodide, again in the presence of copper(I)iodide and bis(triphenylphosphine)palladium(II) chloride under basic conditions in acetonitrile, yielding a 2-amino-3-cyano-4-methyl-5-(substituted-ethynyl)pyridine, for example, 2-amino-3-cyano-4-methyl-5-[(4-trifluoromethylphenyl)ethynyl]-pyridine. The so-prepared pyridine is then cyclized and hydrohalogenated with chloroformamidine hydrochloride in diglyme, affording the corresponding 2,4-diamino-5-methyl-6-[ 1-chloro-2-substituted-ethenyl]-5-deazapteridine, for example, 2,4-diamino-5-methyl-6-[ 1-chloro-2-(4-trifluoromethylphenyl)ethenyl]-5-deazapteridine. Cyclizations with an appropriately substituted 2-amino-3-cyanopyridine and chloroformamidine hydrochloride in diglyme are taught by N. V. Harris et al (J. Med. Chem. 1990, 33, 434–444). Example 10 provides a detailed description of how this reaction is conducted.

In yet another variation in the method to the 2,4-diamino-5,6-disubstituted-5-deazapteridines described above, using a method taught by I. P. Beletskaya et al., (Dokl. Akad. Nauh SSSR 1991, 320(3), 619–622), 2-amino-3-cyano-5-iodo-4-methylpyridine is reacted with an appropriately substituted boronic acid, for example, phenylboronic acid, and gaseous carbon monoxide under basic conditions in the presence of palladium(II) acetate in dioxane, yielding the corresponding 2-amino-3-cyano-5-(substituted carbonyl)-4-methylpyridine, for example, 2-amino-3-cyano-5-phenylcarbonyl-4-methylpyridine. The so-prepared 5-(substituted carbonyl)pyridine is in turn cyclized with guanidine in ethanol, as previously described, yielding the corresponding 2,4-diamino-5-deazapteridine, for example, 2,4-diamino-6-phenylcarbonyl-5-deazapteridine. Example 11 provides a detailed description of how this reaction is conducted.

Other methods known to one skilled in the art are also useful in the preparation of certain compounds within the scope of the present invention. For example, in a method to prepare 2,4-diamino-5-chloro-6-substituted-5-deazapteridine derivatives, 3-cyanopyridine is oxidized with monoperoxyphthalic acid, magnesium salt, hexahydrate, affording 3-cyanopyridine N-oxide. The oxide is in turn nitrated with potassium nitrate and fuming sulfuric acid, yielding 4-nitro-3-cyanopyridine N-oxide. The nitro compound is then chlorinated with phosphorous oxychloride, giving the corresponding 2,4-dichloro-3-cyanopyridine. The dichloro compound is then cyclized with guanidine carbonate in N,N-dimethylformamide, yielding the corresponding 2,4-diamino-5-chloro-5-deazapteridine. The so-prepared 5-deazapteridine is in turn brominated using N-bromosuccinimide in N,N-dimethylformamide, affording 2,4-diamino-6-bromo-5-chloro-5-deazapteridine. This compound is then reacted with an appropriate boronic acid, for example, 3,5-di(trifluoromethyl)phenylboronic acid, yielding the targeted 2,4-diamino-5-chloro-6-substituted-5-deazapteridines, for example, 2,4-diamino-5-chloro-6-[3,5-di(trifluoromethyl)phenyl]-5-deazapteridine. Example 13 provides a detailed description of how this reaction is conducted.

In a method to prepare 5,6,7-tri-substituted-5-deazapteridines, for example, 3-cyano-2-hydroxy-4,6-dimethylpyridine (commercially available) may be brominated with N-bromosuccinimide, affording the corresponding 5-bromo-3-cyano-2-hydroxy-4,6-dimethylpyridine. The bromo compound was in turn may be treated with phosphorus oxychloride in the presence of N,N -dimethylformamide, yielding 2-chloro-5-bromo-3-cyano-4,6-dimethylpyridine. The so-prepared pyridine was cyclized with quanidine carbonate in N,N-dimethylacetamide, yielding the targeted 5,6,7-trisubstituted-5-deazapteridines, for example, 2,4-diamino-6-bromo-5,7-dimethylformamide. Example 19 provides a detailed description of how this reaction is conducted.

The 2,4-diamino-5,6-disubstituted-5-deazapteridines, as depicted above, may be derivatized by methods known to one skilled in the art to provide additional 2,4-diamino-5,6-disubstituted-5-deazapteridines that are within the scope of the present invention. Any of the 2,4-diamino-5,6-disubstituted-5-deazapteridines may be reacted with, for example, a dialkyl dicarbonate in the presence of dimethylaminopyridine, affording a 2,4-di(alkoxycarbonylamino)-6-substituted-5-deazapteridine, for example, 2,4-di[1,1-dimethylethoxy)carbonylamino]-5-methyl-6-[3,5-di(trifluoromethyl)-phenyl]-5-deazapteridine. Example 12 provides a detailed description of how this reaction is conducted.

In addition to the preparation of the 2,4-diamino-5,6-disubstituted-5-deazapteridines as disclosed herein, some of the compounds within the scope of the invention may be purchased from commercial sources. An example of one such source is Dr. John B. Hynes, Dept. of Pharmaceutical Sciences, Medical University of South Carolina, 171 Ashley Avenue, Charleston, S.C. 29425-2303.

EXAMPLES

The following examples are by way of illustration only, and are not intended to limit the scope of the invention claimed herein.

The products of these examples are summarized in Table 1 below.

Example 1

Synthesis of 2,4-diamino-5-methyl-6-phenyl-5-deazapteridine (COMPOUND 28)

Step A Synthesis of ethyl 3-oxo-2-phenylbutanoate as an intermediate

A stirred solution of 10 grams (0.061 mole) of ethyl phenylacetate in 125 mL of tetrahydrofuran is cooled to —78° C., and 33.5 mL (0.067 mole) of lithium diisopropylamide (2M solution in heptane-tetrahydrofuranethylbenzene) is slowly added dropwise at a rate to maintain the reaction mixture temperature below —60° C. Upon completion of addition, the reaction mixture is stirred at —78° C. for about one hour. After this time, 6.5 mL (0.067 mole) of ethyl acetate is added dropwise. Upon completion of addition, the reaction mixture is stirred for about one hour at —78° C. The reaction mixture is then allowed to warm to ambient temperature. After this time the reaction mixture is poured into 200 mL of water, and the mixture is extracted with one 100 mL portion of diethyl ether. The aqueous layer is made acidic with aqueous 10% hydrochloric acid, and then it is extracted with three 150 mL portions of diethyl ether. The combined extracts are dried with magnesium sulfate and filtered. The filtrate is concentrated under reduced pressure, yielding 6.6 grams of ethyl 3-oxo-2-phenylbutanoate. The NMR spectrum is consistent with the proposed structure.

Step B Synthesis of 2,4-diamino-7-hydroxy-5-methyl-6-phenyl-5-deazapteridine as an intermediate (Compound 2A)

A stirred solution of 6.6 grams (0.032 mole) of ethyl 3-oxo-2-phenylbutanoate and 4.0 grams (0.032 mole) of 2,4,6-triaminopyrimidine in diphenyl ether is heated at 195° C. for about two hours. After this time, the reaction mixture is cooled, diluted with methanol, and filtered to collect a solid. The solid is slurried in hot water and is again collected by filtration. The filter cake is washed in turn with hot water, methanol, and then with pentane. The solid is then triturated with hot aqueous 90% N,N-dimethylformamide. The solid is dried, yielding 0.6 gram of 2,4-diamino-7-hydroxy-5-methyl-6-phenyl-5-deazapteridine. The NMR spectrum is consistent with the proposed structure. The reaction is repeated several times.

Step C Synthesis of 2,4-diamino-7-chloro-5-methyl-6-phenyl-5-deazapteridine as an intermediate (Compound 2B)

A stirred solution of 5.1 grams (0.07 mole) of N,N-dimethylformamide in about 35 mL of dry chloroform is cooled to 0° C., and 8.3 grams (0.07 mole) of thionyl chloride in about 10 mL of dry chloroform is added dropwise at a rate to maintain the reaction mixture temperature below 5° C. When the exothermic reaction from the formation of the dimethylformamide-thionyl chloride complex subsides, 2.0 grams (0.007 mole) of 2,4-diamino-7-hydroxy-5-methyl-6-phenyl-5-deazapteridine is added portionwise during a 10–15 minute period. Upon completion of addition, the reaction mixture is allowed to gradually warm to ambient temperature, and then it is heated at reflux for about three hours. The reaction mixture is cooled to ambient temperature and treated with about 30 mL of dilute ethanolic sodium hydroxide, while keeping the reaction mixture temperature at 25°–30° C. A solid is collected by filtration and slurried in about 75 mL of 50% aqueous ammonium hydroxide. The solid is again collected by filtration, washed with water, and dried, yielding 2,4-diamino-7-chloro-5-methyl-6-phenyl-5-deazapteridine.

Step D Synthesis of 2,4-diamino-5-methyl-6-phenyl-5-deazapteridine (Compound 28)

A mixture of 0.23 gram (0.0008 mole) of 2,4-diamino-7-chloro-5-methyl-6-phenyl-5-deazapteridine, 0.2 gram (0.004 mole) of potassium hydroxide and 0.2 gram of 5% palladium on charcoal (catalyst) in about 200 mL of ethanol is subjected to hydrogenolysis using a Parr hydrogenation apparatus, with the hydrogen pressure between about 35–40 psi. Upon completion of the hydrogenolysis, the reaction mixture is filtered to remove the catalyst. The filtrate is concentrated under reduced pressure, yielding 2,4-diamino-5-methyl-6-phenyl-5-deazapteridine.

Example 2

Synthesis of 2,4-diamino-5-methyl-6-(2,5-dimethoxyphenylmethyl)-5-deazapteridine (COMPOUND 90)

Step A Synthesis of ethyl 3-oxo-2-(2,5-dimethoxyphenylmethylidene)-butanoate as an intermediate A stirred solution of 25.0 grams (0.15 mole) of 2,5-dimethoxybenzaldehyde, 22.0 grams (0.17 mole) of ethyl acetoacetate, 2 mL of piperidine, and 3 mL of glacial acetic acid in about 250 mL of toluene is placed in a reaction vessel equipped with a Dean-Stark trap, and heated at reflux for about 12 hours. After this time, the reaction mixture is cooled and washed in turn with water, a cold solution of aqueous 10% hydrochloric acid, aqueous 5% sodium bicarbonate, and aqueous 1% acetic acid. The organic layer is dried with magnesium sulfate and filtered. The filtrate is concentrated under reduced pressure to a residue. The residue is subjected to column chromatography on silica gel. Elution is accomplished using methylene chloride. The column chromatography does not provide product purification as expected. The fractions are recombined and concentrated under reduced pressure to a residual oil. The oil is distilled under vacuum, yielding 32 grams of impure ethyl 3-oxo-2-(2,5-dimethoxyphenylmethylidene)butanoate. The NMR spectrum is consistent with the proposed structure.

Step B Synthesis of ethyl 3-oxo-2-(2,5-dimethoxyphenylmethyl)-butanoate as an intermediate A mixture of 32.0 grams (0.126 mole) of ethyl 3-oxo-2-(2,5-dimethoxyphenylmethylidine)butanoate and 1.5 grams (catalyst) of 5% palladium on charcoal in 250 mL of ethyl acetate is hydrogenated using a Parr hydrogenation apparatus with hydrogen pressure at 20–40 psi. The hydrogenation requires about 12 hours. After this time, the reaction mixture is removed from the hydrogenator and filtered. The filtrate is concentrated under reduced pressure, yielding 32.2 grams of ethyl 3-oxo-2-(2,5-dimethoxyphenylmethyl)butanoate. The NMR spectrum is consistent with the proposed structure.

Step C Synthesis of 2,4-diamino-7-hydroxy-5-methyl-6-(2,5-dimethoxyphenylmethyl)-5-deazapteridine (Compound 8A) as an intermediate This compound is prepared in a manner analogous to that of Step B of Example 1, using 10.0 grams (0.036 mole) of ethyl 3-oxo-2-(2,5-dimethoxyphenylmethyl)butanoate and 4.5 grams (0.036 mole) of 2,4,6-triamino-pyrimidine in diphenyl ether, yielding 5.4 grams of 2,4-diamino-7-hydroxy-5-methyl-6-(2,5-dimethoxyphenylmethyl)-5-deazapteridine. A small sample is triturated with methoxyethanol, filtered, and dried, mp 324°–326° C. The NMR spectrum is consistent with the proposed structure.

Step D Synthesis of 2,4-diamino-7-chloro-5-methyl-6-(2,5-dimethoxyphenylmethyl)-5-deazapteridine (Compound 8B) as an intermediate This compound is prepared in a manner analogous to that of Step C of Example 1, using 5.0 grams (0.015 mole) of 2,4-diamino-7-hydroxy-5-methyl-6-(2,5-dimethoxyphenylmethyl)-5-deazapteridine, 10.9 grams (0.15 mole) of N,N-dimethylformamide, and 17.8 grams (0.15 mole) of thionyl chloride in about 100 mL of dry chloroform, yielding 2,4-diamino-7-chloro-5-methyl-6-(2,5-dimethoxyphenylmethyl)-5-deazapteridine.

Step E Synthesis of 2,4-diamino-5-methyl-6-(2,5-dimethoxyphenylmethyl)-5-deazapteridine (Compound 90)

This compound is prepared in a manner analogous to that of Step D of Example 1, using 0.5 gram (0.0014 mole) of 2,4-diamino-7-chloro-5-methyl-6-(2,5-dimethoxyphenylmethyl)-5-deazapteridine, 0.4 gram (0.007 mole) of potassium hydroxide, and 0.2 gram of 5% palladium on charcoal (catalyst) in ethanol, yielding 2,4-diamino-5-methyl-6-(2,5-dimethoxyphenylmethyl)-5-deazapteridine.

Note: Compound 90 may be prepared as shown above using the method of C. A Nichol et al (J. Med. Chem. 1980, 23, 327–329). Compound 90 used in the present invention is purchased from Dr. John B. Hynes, Dept. of Pharmaceutical Sciences, Medical University of South Carolina, 171 Ashley Avenue, Charleston, S.C. 29425-2303.

Example 3

Synthesis of 2,4-diamino-5-methyl-6-[3,5-di(trifluoromethyl)phenylmethyl]-5-deazapteridine (COMPOUND 89)

Step A Synthesis of ethyl 3-oxo-2-[3,5-di(trifluoromethyl)phenylmethylidene]butanoate as an intermediate This compound is prepared in a manner analogous to that of Step A of Example 2, using 36.3 grams (0.15 mole) of 3,5-di(trifluoromethyl)benzaldehyde, 22.0 grams (0.17 mole) of ethylacetoacetate, 2 mL of piperidine, and 3 mL of glacial acetic acid in 250 mL of toluene, yielding ethyl 3-oxo-2-[3,5-di(trifluoromethyl)phenylmethylidene]butanoate.

Step B Synthesis of ethyl 3-oxo-2-[3,5-di(trifluoromethyl)phenylmethyl]butanoate as an intermediate This compound is prepared in a manner analogous to that of Step B of Example 2, using 44.6 grams (0.126 mole) of ethyl 3-oxo-2-[3,5-di(trifluoromethyl)phenylmethylidene]butanoate and 1.5 grams (catalyst) of 5% palladium on charcoal in 250 mL of ethyl acetate, yielding ethyl 3-oxo-2-[3,5-di(trifluoromethyl)phenylmethyl]butanoate.

Step C Synthesis of 2,4-diamino-7-hydroxy-5-methyl-6-[3,5-di(trifluoromethyl)phenylmethyl]-5-deazapteridine as an intermediate (Compound 7A)

This compound is prepared in a manner analogous to that of Step B of Example 1, using 12.8 grams (0.036 mole) of ethyl 3-oxo-2-[3,5-di(trifluoromethyl)phenylmethyl]butanoate and 4.5 grams (0.036 mole) of 2,4,6-triaminopyrimidine in diphenyl ether, yielding 2,4-diamino-7-hydroxy-5-methyl-6-[3,5-di(trifluoromethyl)phenylmethyl]-5-deazapteridine.

Step D Synthesis of 2,4-diamino-7-chloro-5-methyl-6-[3,5-di(trifluoromethyl)phenylmethyl]-5-deazapteridine (Compound 7B) as an intermediate This compound is prepared in a manner analogous to that of Step C of Example 1, using 6.3 grams (0.015 mole) of 2,4-diamino-7-hydroxy-5-methyl-6-[3,5-di(trifluoromethyl)phenylmethyl]-5-deazapteridine, 10.9 grams (0.15 mole) of N,N-dimethylformamide, and 17.8 grams (0.15 mole) of thionyl chloride in about 100 mL of dry chloroform, yielding 2,4-diamino-7-chloro-5-methyl-6-[3,5-di(trifluoromethyl)phenylmethyl]-5-deazapteridine.

Step E Synthesis of 2,4-diamino-5-methyl-6-[3,5-di(trifluoromethyl)-phenylmethyl]-5-deazapteridine (Compound 89)

This compound is prepared in a manner analogous to that of Step D of Example 1, using 0.6 gram (0.0014 mole) of 2,4-diamino-7-chloro-5-methyl-6-[3,5-di(trifluoromethyl)phenylmethyl]-5-deazapteridine, 0.4 gram (0.007 mole) of potassium hydroxide, and 0.2 gram of 5% palladium on charcoal (catalyst) in ethanol, yielding 2,4-diamino-5-methyl-6-[3,5-di(trifluoromethyl)-phenylmethyl]-5-deazapteridine.

Example 4

Synthesis of 2,4-diamino-5-methyl-6-[3,5-di(trifluoromethyl)phenyl]-5-deazapteridine (COMPOUND 45)

Step A Synthesis of a mixture of 1,1-dicyano-4-ethoxy-3-methyl-1,3-butadiene and 1,1-dicyano-4,4-diethoxy-3-methyl-1-butene as intermediates Under a nitrogen atmosphere, a stirred solution of 4.0 grams (0.038 mole) of 1,1-dicyano-2-methyl-1-propene (commercially available), 6.3 mL (0.038 mole) of triethyl orthoformate, 0.04 gram (catalyst) of zinc chloride, and 7.1 mL (0.075 mole) of acetic anhydride is heated at reflux for 18 hours. After this time an additional 1.3 mL (0.2 equiv.) of triethyl orthoformate and 0.05 gram of zinc chloride are added to the reaction mixture and the heating at reflux is continued for an additional two hours. The reaction mixture is then poured into an aqueous 2M sodium carbonate solution. The aqueous solution is extracted with three 50 mL portions of methylene chloride. The combined extracts are dried with sodium sulfate and filtered. The filtrate is concentrated under reduced pressure, yielding about 6.1 grams of a mixture of 1,1-dicyano-4-ethoxy-3-methyl-1,3-butadiene and 1,1-dicyano-4,4-diethoxy-3-methyl-1-butene.

Note: The mixture of 1,1-dicyano-4-ethoxy-3-methyl-1,3-butadiene and 1,1-dicyano-4, 4-diethoxy-3-methyl-1-butene is prepared using the method of G. S. Ponticello et al (J. Org. Chem. 1978, 43, 2529–2535)

Step B Synthesis of 2-amino-3-cyano-4-methylpyridine as an intermediate

A solution of about 6.1 grams (0.038 mole) of a mixture of 1,1-dicyano-4-ethoxy-3-methyl-1,3-butadiene and 1,1-dicyano-4,4-diethoxy-3-methyl-1-butene in 200 mL of saturated methanolic ammonia is stirred at ambient temperature for about 15 hours. After this time the solvent is removed under reduced pressure, and the residue is partitioned between 160 mL of aqueous 1N hydrochloric acid and 160 mL of ethyl acetate. The aqueous layer is separated and poured into 160 mL of an aqueous solution saturated with sodium bicarbonate. The resultant solid is collected by filtration and dried, yielding about 2.6 grams of 2-amino-3-cyano-4-methylpyridine. Steps A and B are repeated.

Note: The method of E. C. Taylor et al (J. Org. Chem. 1983, 48, 4852–4860) may be used to prepare 2-amino-3-cyano-4-methylpyridine as described above.

Step C Synthesis of 2-amino-5-bromo-3-cyano-4-methylpyridine as an intermediate

A stirred solution of 8.3 grams (0.063 mole) of 2-amino-3-cyano-4-methylpyridine in 125 mL of N,N-dimethylformamide is cooled in an ice bath, and a solution of 11.2 grams (0.063 mole) of N-bromosuccinimide in 125 mL of N,N-dimethylformamide is added dropwise during a 30 minute period, while maintaining the reaction mixture temperature at about 15°–25° C. Upon completion of addition, the reaction mixture is stirred at ambient temperature for about 20 hours. After this time, the reaction mixture is poured into 1 liter of aqueous 3N sodium hydroxide. The mixture is then diluted to a volume of about 1700 mL with distilled water. A solid precipitate is collected by filtration and dried under reduced pressure, yielding 2-amino-5-bromo-3-cyano-4-methylpyridine.

Step D Synthesis of 2-amino-3-cyano-4-methyl-5-[3,5-di(trifluoromethyl)phenyl]pyridine as an intermediate A stirred solution of 1.7 grams (0.008 mole) of 2-amino-5-bromo-3-cyano-4-methylpyridine, 3.2 grams (0.012 mole) of 3,5-di(trifluoromethyl)-phenylboronic acid (commercially available), 4.3 grams (0.031 mole) of potassium carbonate and 0.3 gram of tetrakis(triphenylphosphine)palladium(0) in 150 mL of toluene is heated at 90° C. for about 20 hours. After this time, the reaction mixture is stirred with 100 mL of water, and the organic layer is separated. The organic layer is concentrated under reduced pressure, yielding 2-amino-3-cyano-4-methyl-5-[3,5-di(trifluoromethyl)-phenyl]pyridine.

Step E Synthesis of 2,4-diamino-5-methyl-6-[3,5-di(trifluoromethyl)-phenyl]-5-deazapteridine (Compound 45)

A stirred mixture of 1.7 grams (0.005 mole) of 2-amino-3-cyano-4-methyl-5-[3,5-di(trifluoromethyl)phenyl]pyridine and 0.6 gram (0.010 mole) of guanidine (prepared from 1.0 gram (0.010 mole) of guanidine hydrochloride and 0.5 gram (0.011 mole) of metallic sodium in about 20 mL of anhydrous methanol, filtered to remove sodium chloride) is heated at reflux for about 99 hours. The reaction mixture is then cooled to ambient temperature and concentrated under reduced pressure to a small volume. The concentrate is then cooled to about −20° C. and filtered. The collected solid is washed in turn with water, 10 mL of cold (−20° C.) methanol, and diethyl ether, yielding 2,4-diamino-5-methyl-6-[3,5-di(trifluoromethyl)phenyl]-5-deazapteridine.

Note: The method of E. C. Taylor et al (J. Org. Chem. 1983, 48, 4852–4860) may be used to prepare the targeted 2,4-diamino-5-methyl-6-[3,5-di(trifluoromethyl)phenyl]-5-deazapteridine (Compound 45) as described above.

Example 5

Synthesis of 2,4-diamino-5-methyl-6-(3-fluoro-5-trifluoromethylphenyl)-5-deazapteridine (COMPOUND 44)

Step A Synthesis of 3-fluoro-5-trifluoromethylphenylboronic acid as an intermediate A crystal of iodine and 0.5 gram (0.021 mole) of magnesium turnings are placed in a reaction vessel containing 10 mL of tetrahydrofuran. To this is added dropwise 2 mL of a solution of 5.0 grams (0.021 mole) of 3-fluoro-5-trifluoromethylphenyl bromide (commercially available) in 65 mL of tetrahydrofuran. The Grignard formation is initiated by warming the reaction vessel to about 45° C. The remaining 3-fluoro-5-trifluoromethylphenyl bromide-tetrahydrofuran solution is added portionwise at a rate which maintained gentle reflux of the reaction mixture.

In a second reaction vessel, 40 mL of tetrahydrofuran is cooled to −78° C., and 2.3 mL (0.021 mole) of trimethyl borate is added dropwise as the Grignard reagent of 3-fluoro-5-trifluoromethylphenyl bromide prepared above is transferred into the second reaction vessel using a cannula. The temperature of the reaction mixture is maintained below −60° C. during the additions. Upon completion of the additions, the reaction mixture is again cooled to −78° C., where it is stirred for about 45 minutes. After this time, the reaction mixture is allowed to warm to ambient temperature. The reaction mixture is then poured into about 200 mL of water and is made acidic with aqueous 5% hydrochloric acid. The mixture is extracted with four 100 mL portions of ethyl acetate. The combined extracts are dried with magnesium sulfate and filtered. The tiltrate is concentrated under reduced pressure, yielding 3.3 grams of 3-fluoro-5-trifluoromethylphenylboronic acid, mp 167°–168° C. The NMR spectrum is consistent with the proposed structure.

Step B Synthesis of 2-amino-3-cyano-4-methyl-5-[3-fluoro-5-trifluoromethylphenyl]pyridine as an intermediate This compound is prepared in a manner analogous to that of Step D of Example 4, using 1.7 grams (0.008 mole) of 2-amino-5-bromo-3-cyano-4-methylpyridine, 2.5 grams (0.012 mole) of 3-fluoro-5-trifluoromethylphenylboronic acid, 4.3 grams (0.031 mole) of potassium carbonate and 0.3 gram of tetrakis(triphenylphosphine)palladium(0) in 150 mL of toluene, yielding 2-amino-3-cyano-4-methyl-5-[3-fluoro-5-trifluoromethylphenyl]pyridine.

Step C Synthesis of 2,4-diamino-5-methyl-6-(3-fluoro-5-trifluoro-methylphenyl)-5-deazapteridine (Compound 44)

This compound is prepared in a manner analogous to that of Step E of Example 4, using 1.5 grams (0.005 mole) of 2-amino-3-cyano-4-methyl-5-[3-fluoro-5-trifluoromethylphenyl]pyridine and 0.6 gram (0.010 mole) of guanidine (prepared from 1.0 gram (0.010 mole) of guanidine hydrochloride and 0.5 gram (0.011 mole) of metallic sodium in about 20 mL of anhydrous methanol, filtered to remove sodium chloride), yielding 2,4-diamino-5-methyl- 6-(3-fluoro-5-trifluoromethylphenyl)-5-deazapteridine

Example 6

Synthesis of
2,4-diamino-5-methyl-6-[3-(4-chlorophenyl)-phenyl]-5-deazapteridine (COMPOUND 66)

Step A Synthesis of 3-(4-chlorophenyl)phenyl bromide as an intermediate

This compound is prepared in a manner analogous to that of Step D of Example 4, using 6.9 grams (0.044 mole) of 4-chlorophenylboronic acid (commercially available), 25.0 grams (0.100 mole) of 1,3-dibromobenzene, 0.2 gram (catalyst) of tetrakis(triphenylphosphine)palladium(0), 75 mL of aqueous 2M sodium carbonate, and 75 mL of toluene, yielding 3-( 4-chlorophenyl)phenyl bromide.

Step B Synthesis of 3-(4-chlorophenyl)phenylboronic acid as an intermediate

A stirred solution of 6.9 grams (0.026 mole) of 3-(4-chlorophenyl)-phenyl bromide in 150 mL of tetrahydrofuran is cooled to −80° C., and 11.5 mL of n-butyllithium in hexanes (2.5 Molar-0.029 mole) is added dropwise during a 15 minute period, while maintaining the reaction mixture temperature at about −70° C. Upon completion of the addition, the reaction mixture is stirred at −80° C. for 15 minutes. After this time, 17.5 mL (0.076 mole) triisopropyl borate is added during a one minute period. The reaction mixture is then allowed to warm slowly to ambient temperature during a three hour period, where it is stirred for an additional one hour. After this time, the reaction mixture is concentrated under reduced pressure to a volume of about 50 mL. The concentrate is then poured into 500 mL of icewater. The mixture is then made acidic with about 26 mL of aqueous 2N hydrochloric acid. The mixture is then filtered, collecting 3-(4-chlorophenyl)-phenylboronic acid.

Note: The method of Thompson and Gaudino [JOC., 49, 1984, 5237 −5243 ] may be used to prepare 3-(4-chlorophenyl)phenylboronic acid, as shown above in Step B.

Step C Synthesis of 2-amino-3-cyano-4-methyi-5-[3-(4-chlorophenyl) phenyl]pyridine as an intermediate This compound is prepared in a manner analogous to that of Step D of Example 4, using 1.7 grams (0.008 mole) of 2-amino-5-bromo-3-cyano-4-methylpyridine, 2.9 grams (0.012 mole) of 3-(4-chlorophenyl)phenylboronic acid, 4.3 grams (0.031 mole) of potassium carbonate and 0.3 gram of tetrakis(triphenylphosphine)palladium(0) in 150 mL of toluene, yielding 2-amino-3 -cyano-4-methyl-5-[3-( 4-chlorophenyl)phenyl]pyridine.

Step D Synthesis of 2,4-diamino-5-methyl-6-[3-(4-chlorophenyl)-phenyl]-5-deazapteridine (Compound 66)

This compound is prepared in a manner analogous to that of Step E of Example 4, using 1.6 grams (0.005 mole) of 2-amino-3-cyano-4-methyl-5-[3-(4-chlorophenyl)phenyl] pyridine and 0.6 gram (0.010 mole) of guanidine (prepared from 1.0 gram (0.010 mole) of guanidine hydrochloride and 0.5 gram (0.011 mole) of metallic sodium in about 20 mL of anhydrous methanol, filtered to remove sodium chloride), yielding 2,4-diamino-5-methyl-6 -[3-(4-chlorophenyl)phenyl]-5-deazapteridine.

Example 7

Synthesis of 2,4-diamino-5-methyl-6-[3-fluoro-5-(4-fluorophenoxy)phenyl ]-5-deazapteridine (COMPOUND 82)

Step A Synthesis of 3-fluoro-5-(4-fluorophenoxy)phenyl bromide as an intermediate Under a nitrogen atmosphere, a solution of 11.9 grams (0.106 mole) of 4-fluorophenol in 50 mL of diglyme is stirred, and 24.1 mL (0.106 mole) of methanolic 25% sodium methoxide is added dropwise. Upon completion of addition, the reaction mixture is heated to about 165° C. to remove methanol. After the methanol is removed, the heating is ceased, and 26.9 grams (0.106 mole) of 1,3-dibromo-5-fluorobenzene (commercially available) and 1.3 grams of cuprous bromide are added. Upon completion of the additions, the reaction mixture is heated to reflux where it is stirred for about 21 hours. The reaction mixture is then cooled and filtered. The filter cake is washed with diethyl ether, and the wash is combined with the filtrate. The combination is washed with two 20 mL portions of aqueous 20% sodium hydroxide, and then with two 75 mL portions of an aqueous solution saturated with sodium chloride. The organic layer is dried with magnesium sulfate and filtered. The filtrate is concentrated under reduced pressure, yielding 3-fluoro-5-(4-fluorophenoxy)phenyl bromide.

Step B Synthesis of 3-fluoro-5-(4-fluorophenoxy)phenylboronic acid as an intermediate This compound is prepared in a manner analogous to that of Step B of Example 6, using 9.1 grams (0.032 mole) of 3-fluoro-5-(4-fluorophenoxy)-phenyl bromide, 14 mL (0.035 mole) of n-butyllithium (2.5M in hexanes), and 10.4 mL (0.095 mole) of trimethyl borate in 100 mL of tetrahydrofuran, yielding 3-fluoro-5-(4-fluorophenoxy)phenylboronic acid.

Step C Synthesis of 2-amino-3-cyano-4-methyl-5-[3-fluoro-5-(4-fluorophenoxy)phenyl ]pyridine as an intermediate This compound is prepared in a manner analogous to that of Step D of Example 4, using 1.7 grams (0.008 mole) of 2-amino-5-bromo-3-cyano-4-methylpyridine, 3.0 grams (0.012 mole) of 3-fluoro-5-(4-fluorophenoxy)-phenylboronic acid, 4.3 grams (0.031 mole) of potassium carbonate and 0.3 gram of tetrakis(triphenylphosphine)palladium(0) in 150 mL of toluene, yielding 2-amino-3-cyano-4-methyl-5-[3-fluoro-5-(4-fluorophenoxy)phenyl]-pyridine.

Step D Synthesis of 2,4-diamino-5-methyl-6-[3-fluoro-5-(4-fluoro-phenoxy) phenyl]-5-deazapteridine (Compound 82)

This compound is prepared in a manner analogous to that of Step E of Example 4, using 1.7 grams (0.005 mole) of 2-amino-3-cyano-4-methyl-5-[3-fluoro- 5-(4-fluorophenoxy)phenyl]pyridine and 0.6 gram (0.010 mole) of guanidine (prepared from 1.0 gram (0.010 mole) of guanidine hydrochloride and 0.5 gram (0.011 mole) of metallic sodium in about 20 mL of anhydrous methanol, filtered to remove sodium chloride), yielding 2,4-diamino-5-methyl-6-[3-fluoro-5-(4-fluorophenoxy)phenyl]-5-deazapteridine.

Example 8

Synthesis of
2,4-diamino-5-methyl-6-(6-chloro-2,3-dihydro-2,2-dimethylbenzofuran-4-yl)-5-deazapteridine (COMPOUND 104)

Step A Synthesis of 2-methyl-3-(3-chloro-2-cyanophenoxy)-1-propene as an intermediate A solution of 30.0 grams (0.174 mole) of 2,6-dichlorobenzonitrile and 14.7 mL (0.174 mole) of 2-methyl-2-propen-1-ol in 200 mL of dimethyl sulfoxide is stirred, and 12.7 grams (0.191 mole) of 85% potassium hydroxide is added portionwise during a 5 minute period. During the addition, the reaction mixture temperature rises from 20° C. to about 35° C. Upon completion of the addition, the reaction mixture is stirred at ambient temperature for about 18 hours. After this time the reaction mixture is poured into 600 mL of water. The mixture is filtered to collect a solid. The solid is washed with water and dried under vacuum, yielding 33.9 grams of 2-methyl-3-(3-chloro-2-cyanophenoxy)-1-propene. The NMR spectrum is consistent with the proposed structure.

Step B Synthesis of 6-chloro-7-cyano-2,3-dihydro-2,2-dimethylbenzofuran as an intermediate A stirred mixture of 33.9 grams (0.163 mole) of 2-methyl-3-(3-chloro-2-cyanophenoxy)-1-propene and 0.2 gram (0.0017 mole) of magnesium chloride is warmed to 180° C. during a one hour period, where it is stirred for about six hours. The product, which sublimed to the top of the reaction vessel, is subjected to column chromatography on silica gel. Elution is accomplished using 1:1 methylene chloride and petroleum ether. The product-containing fractions are combined and concentrated under reduced pressure, yielding 25.8 grams of 6-chloro-7-cyano-2,3-dihydro-2,2-dimethylbenzofuran. The NMR spectrum is consistent with the proposed structure.

Step C Synthesis of 7-aminocarbonyl-6-chloro-2,3-dihydro-2,2-dimethylbenzofuran as an intermediate A stirred solution of 10.0 grams (0.048 mole) of 6-chloro-7-cyano-2,3-dihydro-2,2-dimethylbenzofuran in 200 mL of 2-methyl-2-propanol is warmed to reflux, and 9.5 grams (0.17 mole) of 85% potassium hydroxide is added in one portion. Upon completion of addition, the reaction mixture is heated at reflux for about 75 minutes. The reaction mixture is then cooled and poured into 400 mL of water that is cooled in an ice bath. The resultant solid is collected by filtration and dried under vacuum, yielding 8.2 grams of 7-aminocarbonyl-6-chloro-2,3-dihydro-2,2-dimethylbenzofuran. The NMR spectrum is consistent with the proposed structure.

Step D Synthesis of 7-amino-6-chloro-2,3-dihydro-2,2-dimethylbenzofuran as an intermediate A stirred solution of 5.8 grams (0.145 mole) of sodium hydroxide in 100 mL of water is cooled to 0° C., and 7.3 grams (0.045 mole) of bromine is added dropwise during a 5 minute period. Upon completion of addition, the mixture is stirred for 5 minutes, and an emulsion of 8.2 grams (0.036 mole) of 7-aminocarbonyl-6-chloro-2,3-dihydro-2,2-dimethylbenzofuran in 75 mL of dioxane is added portionwise during a 15 minute period. Upon completion of addition, the reaction mixture is stirred at 0° C. for one hour. The reaction mixture is warmed to 75° C. during a two hour period, where it is stirred for 19 hours. After this time the reaction mixture is cooled and poured into 300 mL of water. The mixture is then extracted with two 200 mL portions of ethyl acetate. The combined extracts are washed with an aqueous solution saturated with sodium chloride and dried with magnesium sulfate. The mixture is filtered and concentrated under reduced pressure to a residue. The residue is subjected to column chromatography on silica gel. Elution is accomplished using methylene chloride. The product containing fractions are combined and concentrated under reduced pressure, yielding 4.5 grams of 7-amino-6-chloro-2,3-dihydro-2,2-dimethylbenzofuran. The NMR spectrum is consistent with the proposed structure.

Step E Synthesis of 7-amino-4-bromo-6-chloro-2,3-dihydro-2,2-dimethylbenzofuran as an intermediate This compound is prepared in a manner analogous to that of Step C of Example 1, using 4.5 grams (0.023 mole) of 7-amino-6-chloro-2,3-dihydro-2,2-dimethylbenzofuran and 4.1 grams (0.023 mole) of N-bromosuccinimide in 50 mL of N,N-dimethylformamide. The yield of 7-amino-4-bromo-6-chloro-2,3-dihydro-2,2-dimenthylbenzofuran is 5.1 grams. The NMR spectrum is consistent with the proposed structure.

Step F Synthesis of 4-bromo-6-chloro-2,3-dihydro-2,2-dimethylbenzofuran as an intermediate A stirred solution of 5.1 grams (0.018 mole) of 7-amino-4-bromo-6-chloro-2,3-dihydro-2,2-dimethylbenzofuran and 25 mL of toluene in 100 mL of ethanol is cooled in an ice bath, and 2 mL (0.036 mole) of concentrated sulfuric acid is added slowly. Upon completion of addition, 2.0 grams (0.029 mole) of sodium nitrite is then added. The ice bath is then removed, and the reaction mixture is warmed to 75° C., where it is stirred for 30 minutes. After this time the reaction mixture is warmed to 95° C., where it stirred for one hour. The reaction mixture is then cooled and poured into 200 mL of water. The mixture is extracted with two 150 mL portions of diethyl ether. The combined extracts are dried with magnesium sulfate and filtered. The filtrate is concentrated under reduced pressure to a residue. The residue is subjected to column chromatography on silica gel. Elution is accomplished using petroleum ether. The product-containing fractions are combined and concentrated under reduced pressure, yielding 3.6 grams of 4-bromo-6-chloro-2,3-dihydro-2,2-dimethylbenzofuran. The NMR spectrum is consistent with the proposed structure.

Step G Synthesis of 6-chloro-2,3-dihydro-2,2-dimethylbenzofuran-4-ylboronic acid as an intermediate This compound is prepared in a manner analogous to that of Step B of Example 6, using 3.6 grams (0.014 mole) of 4-bromo-6-chloro-2,3-dihydro-2,2-dimethylbenzofuran, 5.5 mL (0.014 mole) of n-butyllithium (2.5M in hexanes), and 4.7 mL (0.042 mole) of trimethyl borate in 75 mL of tetrahydrofuran. The yield of 6-chloro-2,3-dihydro-2,2-dimethylbenzofuran-4-ylboronic acid is 3.0 grams. The NMR spectrum is consistent with the proposed structure.

Step H Synthesis of 2-amino-3-cyano-4-methyl-5-(6-chloro-2,3-dihydro-2, 2-dimethylbenzofuran-4-yl)pyridine as an intermediate This compound is prepared in a manner analogous to that of Step D of Example 4, using 1.7 grams (0.008 mole) of 2-amino-5-bromo-3-cyano-4-methylpyridine, 2.7 grams (0.012 mole) of 6-chloro-2,3-dihydro-2,2-dimethylbenzofuran-4-ylboronic acid, 4.3 grams (0.031 mole) of potassium carbonate and 0.3 mL (catalyst) of tetrakis(triphenylphosphine)palladium(0) in 150 mL of toluene, yielding 2-amino-3-cyano-4-methyl-5-(6-chloro-2,3-dihydro-2, 2-dimethylbenzofuran-4-yl)pyridine.

Step I Synthesis of 2,4-diamino-5-methyl-6-(6-chloro-2,3-dihydro-2, 2-dimethylbenzofuran-4-yl)-5-deazapteridine (Compound 104)

This compound is prepared in a manner analogous to that of Step E of Example 4, using 1.6 grams (0.005 mole) of 2-amino-3-cyano-4-methyl-5-(6-chloro-2,3-dihydro-2,2-dimethylbenzofuran-4-yl)pyridine and 0.6 gram (0.010 mole) of guanidine (prepared from 1.0 gram (0.010 mole) of guanidine hydrochloride and 0.5 gram (0.011 mole) of metallic sodium in about 20 mL of anhydrous methanol, filtered to remove sodium chloride), yielding 2,4-diamino-5-methyl-6-(6-chloro-2,3-dihydro-2,2-dimethylbenzofuran-4-yl)-5-deazapteridine.

Example 9

Synthesis of 2,4-diamino-5-methyl-6-(2,3-dihydro-2,2-dimethyl-3-benzofuranon-4-yl)-5-deazapteridine

(COMPOUND 106)

Step A Synthesis of 7-amino-4-bromo-2,3-dihydro-2,2-dimethylbenzofuran as an intermediate A stirred solution of 10.0 grams (0.061 mole) of 7-amino-2,3-dihydro-2,2-dimethylbenzofuran in 150 mL of N,N-dimethylformamide is cooled in an ice-water bath, and a solution of 10.9 grams (0.061 mole) of N-bromosuccinimide in 50 mL of N,N-dimethylformamide is added in one portion. Upon completion of addition, the reaction mixture is maintained in the ice-water bath for about one hour. After this time the reaction mixture is poured into about 600 mL of water. The mixture is then extracted with two 200 mL portions of diethyl ether. The combined extracts are washed with two 100 mL portions of an aqueous 10% lithium chloride solution. The organic layer is dried with magnesium sulfate and filtered. The filtrate is concentrated under reduced pressure, yielding 12.3 grams of 7-amino-4-bromo-2,3-dihydro-2,2-dimethylbenzofuran. The NMR spectrum is consistent with the proposed structure.

Step B Synthesis of 4-bromo-2,3-dihydro-2,2-dimethylbenzofuran as an intermediate A stirred solution of 12.3 grams (0.051 mole) of 7-amino-4-bromo-2,3-dihydro-2,2-dimethylbenzofuran and 30 mL of toluene in 200 mL of ethanol is cooled in an ice-bath, and 5.6 mL (0.102 mole) of concentrated sulfuric acid is added slowly, followed by 5.6 grams (0.082 mole) of sodium nitrite. Upon completion of addition, the ice-bath is removed, and the reaction mixture is warmed to 50° C. The reaction mixture temperature is then brought to about 75° C., where it is stirred for 30 minutes. After this time the reaction mixture is heated at reflux for one hour and then is poured into 200 mL of water. The mixture is extracted with two 150 mL portions of diethyl ether. The combined extracts are dried with magnesium sulfate and filtered. The filtrate is concentrated under reduced pressure to a residual oil. The oil is subjected to column chromatography of on silica gel. Elution is accomplished using petroleum ether. The product-containing fractions are combined and concentrated under reduced pressure, yielding 3.6 grams of 4-bromo-2,3-dihydro-2,2-dimethylbenzofuran. The NMR spectrum is consistent with the proposed structure.

Step C Synthesis of 4-bromo-2,3-dihydro-2,2-dimethyl-3-benzofuranone as an intermediate Under a nitrogen atmosphere, a stirred solution of 3.0 grams (0.013 mole) 4-bromo-2,3-dihydro-2,2-dimethylbenzofuran, 10.7 grams (0.039 mole) of potassium persulfate, and 3.3 grams (0.013 mole) of copper(II) sulfate pentahydrate in 30 mL of water and 30 mL of acetonitrile is heated at reflux for one hour. After this time the reaction mixture is poured into 200 mL of water. The mixture is then extracted with one 200 mL portion of diethyl ether. The extract is dried with magnesium sulfate and filtered. The filtrate is concentrated under reduced pressure to a residual oil. The oil is subjected to column chromatography on silica gel. Elution is accomplished using 1:1 petroleum ether and methylene chloride. The product-containing fractions are combined and concentrated under reduced pressure, yielding 2.1 grams of 4-bromo-2,3-dihydro-2,2-dimethyl-3-benzofuranone. The NMR spectrum is consistent with the proposed structure.

Step D Synthesis of (2,3-dihydro-2,2-dimethyl-3-benzofuranon-4-yl) trimethyltin as an intermediate Under a nitrogen atmosphere, a stirred solution of 2.1 grams (0.009 mole) of 4-bromo-2,3-dihydro-2,2-dimethyl-3-benzofuranone, 4.3 grams (0.013 mole) of hexamethylditin, and 0.5 gram (catalyst) of tetrakis(triphenylphosphine)palladium(0) in 50 mL of toluene is heated at reflux for one hour. After this time the reaction mixture is allowed to cool to ambient temperature where it stands for about 16 hours. The reaction mixture is then filtered through diatomaceous earth, and the filtrate is concentrated under reduced pressure to a residue. The residue is purified by column chromatography, yielding (2,3-dihydro-2,2-dimethyl-3-benzofuranon-4-yl) trimethyltin.

Note: The method of A. Pidcock et al (J. Organometallic Chem., 215, 1981, 49–58) may be used to prepare (2,3-dihydro-2,2-dimethyl-3-benzofuranon-4-yl)trimethyltin as described above.

Step E Synthesis of 2-amino-3-cyano-5-iodo-4-methylpyridine as an intermediate

This compound is prepared in a manner analogous to that of Step C of Example 4, using 8.3 grams (0.063 mole) of 2-amino-3-cyano-4-methylpyridine (prepared as in Step B of Example 4) and 14.2 grams (0.063 mole) of N-iodosuccinimide in 250 mL of N,N-dimethylformamide, yielding 2-amino-3-cyano-5-iodo-4-methylpyridine.

Step F Synthesis of 2-amino-3-cyano-4-methyl-5-(2,3-dihydro-2,2-dimethyl-3-benzofuranon-4-yl)pyridine as an intermediate Under a nitrogen atmosphere, a stirred solution of 1.8 grams (0.007 mole) of 2-amino-3-cyano-5-iodo-4-methylpyridine, 2.3 grams (0.007 mole) of (2,3-dihydro-2,2-dimethyl-3-benzofuranon-4-yl)trimethyltin (prepared in Step D of this Example), and 0.5 gram (catalyst) of tetrakis(triphenylphosphine)palladium(0) in 25 mL of toluene is heated at reflux for about 22 hours. After this time the reaction mixture is cooled to ambient temperature and diluted with 50 mL of ethyl acetate. The mixture is filtered through diatomaceous earth, and the filtrate is concentrated under reduced pressure to a residue. The residue is purified using column chromatography, yielding 2-amino-3-cyano-4-methyl-5-(2,3-di hydro-2,2-dimethyl-3-benzofuranon-4-yl)pyridine.

Step G Synthesis of 2,4-diamino-5-methyl-6-(2,3-dihydro-2,2-dimethyl-3-benzofuranon-4-yl)-5-deazapteridine (Compound 106)

This compound is prepared in a manner analogous to that of Step E of Example 4, using 1.5 grams (0.005 mole) of 2-amino-3-cyano-4-methyl-5-(2,3-dihydro-2,2-dimethyl-3-benzofuranon-4-yl)pyridine and 0.6 gram (0.010 mole) of guanidine (prepared from 1.0 gram (0.010 mole) of guanidine hydrochloride and 0.5 gram (0.011 mole) of metallic sodium in about 20 mL of anhydrous methanol, filtered to remove sodium chloride), yielding 2,4-diamino- 5-methyl-6-(2,3-dihydro-2,2-dimethyl-3-benzofuranon-4-yl)-5-deazapteridine.

Example 10

Synthesis of 2,4diamino-5-methyl-6-[1-chloro-2-(4-trifluoromethylphenyl) thenyl]-5-deazapteridine

(COMPOUND 165)

Step A Synthesis of 2-amino-3-cyano-4-methyl-5-(trimethylsilyl-ethynyl) pyridine as an intermediate A solution of 5.1 grams (0.020 mole) of 2-amino-3-cyano-5-iodo-4-methylpyridine (prepared as in Step E of Example 9) and 4.2 mL (0.030 mole) of trimethylsilylacetylene in 40 mL of acetonitrile is stirred, and 10.5 mL (0.078 mole) of triethylamine, 0.1 gram of copper(I) iodide, and 0.3 gram of bis(triphenyl-phosphine)palladium(II) chloride are added in order. Upon completion of addition, the reaction mixture is stirred at ambient temperature for about 20 hours and then is warmed to 70 ° C., where it stirred for about 7.5 hours. The reaction is monitored by thin layer chromatography. Upon completion of the reaction, the reaction mixture is concentrated under reduced pressure to a residue. The residue is dissolved in ethyl acetate, and the solution is washed with 50 mL of aqueous dilute hydrochloric acid. The organic layer is dried with magnesium sulfate and filtered. The filtrate is concentrated under reduced pressure, yielding 2-amino-3-cyano-4-methyl-5-(trimethylsilylethynyl) pyridine.

Step B Synthesis of 2-amino-3-cyano-4-methyl-5-ethynylpyridine as an intermediate A mixture of 2.8 grams (0.012 mole) of 2-amino-3-cyano-4-methyl-5-(trimethylsilylethynyl)pyridine and 1.8 grams (0.012 mole) of potassium carbonate in 100 mL of methanol is stirred at ambient temperature for one hour. The reaction mixture is then concentrated under reduced pressure to a residue. The residue is taken up in about 150 mL of water, and the solution is extracted with two 250 mL portions of diethyl ether. The combined extracts are dried with magnesium sulfate and filtered. The filtrate is concentrated under reduced pressure, yielding 2-amino-3-cyano-4-methyl-5-ethynylpyridine.

Step C Synthesis of 2-amino-3-cyano-4-methyl-5-[(4-trifluoromethylphenyl)ethynyl]pyridine as an intermediate A solution of 1.6 grams (0.010 mole) of 2-amino-3-cyano-4-methyl-5-ethynylpyridine, 3.8 grams (0.014 mole) of 4-trifluoromethylphenyl iodide (commercially available), 3.5 grams (0.035 mole) of triethylamine, 0.3 gram (catalyst) of bis(triphenylphosphine)palladium(II) chloride, and 0.3 gram (catalyst) of copper(I)iodide in 75 mL of acetonitrile is stirred at ambient temperature for about 18 hours. After this time the reaction mixture is concentrated under reduced pressure to a residue. The residue is partitioned between ethyl acetate and aqueous 1N hydrochloric acid. The aqueous layer and the organic layer are separated, and the aqueous layer is washed with ethyl acetate. The ethyl acetate wash is combined with the organic layer, and the combination is washed with an aqueous solution of 10% lithium chloride. The organic layer is dried with magnesium sulfate and filtered. The filtrate is concentrated under reduced pressure, yielding 2-amino- 3-cyano-4-methyl-5-[(4-trifluoromethylphenyl)ethynyl]pyridine.

Step D Synthesis of chloroformamidine hydrochloride as an intermediate

Diethyl ether, 600 mL, is cooled in an ice-bath and saturated with about 50 grams of hydrogen chloride gas. With vigorous stirring, a solution of 26.4 grams (0.628 mole) of cyanamide in 500 mL of diethyl ether is added during a 15 minute period. Upon completion of addition, the ice-bath is removed, and the reaction mixture is allowed to stir for about 15 minutes. A white solid precipitate is collected by filtration and washed with diethyl ether. The solid is dried under reduced pressure, yielding 50.3 grams of chloroformamidine hydrochloride.

Step E Synthesis of 2,4-diamino-5-methyl-6-[ 1-chloro-2-(4-trifluoromethylphenyl) ethenyl]-5-deazapteridine (Compound 165)

A stirred mixture of 0.9 gram (0.003 mole) of 2-amino-3-cyano-4-methyl- 5-[(4-trifluoromethylphenyl)ethynyl]pyridine (prepared in Step C of this Example) and 0.3 gram (0.003 mole) of chloroformamidine hydrochloride in 11 mL of diglyme is gradually warmed to 165° C. during a 1.5 hour period. The heterogeneous mixture is maintained at 165° C. for about 4.5 hours. After this time, the reaction mixture is cooled and diluted with 200 mL of diethyl ether. The resultant precipitate, which is the hydrochloride salt of the sought-after product, is collected by filtration. The hydrochloride salt is converted to the free base by cooling it in an ice-water bath and stirring it with about 30 mL of concentrated ammonium hydroxide during a 1 hour period. The resultant solid is collected by filtration, yielding 2,4-diamino-5-methyl-6-[ 1-chloro-2-(4-trifluoromethylphenyl)ethenyl]-5-deazapteridine.

Example 11

Synthesis of
2,4-diamino-5-methyl-6-phenylcarbonyl-
5-deazapteridine (COMPOUND 172)

Step A Synthesis of 2-amino-3-cyano-4-methyl-5-phenylcarbonylpyridine as an intermediate A solution of 4.9 grams (0.019 mole) of 2-amino-3-cyano-5-iodo-4-methylpyridine (prepared as in Step E of Example 9) in 75 mL of dioxane is stirred, and gaseous carbon monoxide is bubbled in during a 15 minute period. While maintaining a carbon monoxide atmosphere, 4.7 grams (0.039 mole) of phenylboronic acid (commercially available), 6.8 mL (0.048 mole) of triethylamine, and 0.5 gram (catalyst) of palladium(II) acetate are in turn added. To maintain the carbon monoxide atmosphere, a balloon filled with carbon monoxide gas is then attached to the reaction vessel. The reaction mixture is then warmed to 65° C. where it is stirred for about 20 hours. The reaction mixture is then poured into a mixture of 300 mL of water and 100 mL of aqueous saturated sodium chloride solution. This mixture is extracted with two 150 mL portions of ethyl acetate. The combined extracts are dried with magnesium sulfate and filtered. The filtrate is concentrated under reduced pressure to a residue. The residue is purified using column chromatography, yielding 2-amino-3-cyano-4-methyl-5-phenylcarbonylpyridine.

Step B Synthesis of 2,4-diamino-5-methyl-6-phenylcarbonyl-5-deazapteridine (Compound 172)

This compound is prepared in a manner analogous to that of Step E of Example 4, using 1.2 grams (0.005 mole) of 2-amino-3-cyano-4-methyl-5-phenylcarbonylpyridine and 0.6 gram (0.010 mole) of guanidine (prepared from 1.0 gram (0.010 mole) of guanidine hydrochloride and 0.5 gram (0.011 mole) of metallic sodium in about 20 mL of anhydrous methanol, filtered to remove sodium chloride), yielding 2,4-diamino-5-methyl-6-phenylcarbonyl-5-deazapteridine.

Example 12

Synthesis of
2,4-di[(1,1-dimethylethoxy)carbonylamino]-5-methyl-
6-[3,5-di(trifluoromethyl)phenyl]-
5-deazapteridine (COMPOUND 137)

A stirred mixture of 1.9 grams (0.0050 mole) of 2,4-diamino-5-methyl-6-[3,5-di(trifluoromethyl)phenyl]-5-deazapteridine (Compound 45-prepared in Example 4), 0.06 gram (0.0005 mole) of dimethylaminopyridine, and 10.00 grams (0.0458 mole) of di-tert-butyl dicarbonate is heated at 75° C. for about 6 hours. The reaction mixture is cooled and dissolved in ethyl acetate. The solution is passed through a column of silica gel. The eluate is concentrated under reduced pressure to a residue. The residue is triturated with hexane to remove unreacted di-tert-butyl dicarbonate, yielding 2,4-di[ ( 1,1 -dimethylethoxy)carbonylamino]-5-methyl-6-[ 3,5-di (trifluoromethyl)phenyl]-5-deazapteridine.

Example 13

Synthesis of
2,4-diamino-5-chloro-6-[3,5-di(trifluoro-methyl) phenyl]-5-deazapteridine (COMPOUND 25)

Step A Synthesis of 3-cyanopyridine N-oxide as an intermediate

A mixture of 20.0 grams (0.194 mole) of 3-cyanopyridine and 142.5 grams (0.288 mole) of monoperoxyphthalic acid, magnesium salt, hexahydrate (80% pure) in 300 mL of methylene chloride is stirred at ambient temperature for about 24 hours. After this time, the mixture is filtered, and the filtrate is concentrated under reduced pressure, yielding 3-cyanopyridine N-oxide.

Step B Synthesis of 4-nitro-3-cyanopyridine N-oxide as an intermediate

One hundred fifty mL of stirred 15% fuming nitric acid is cooled to 5°–10° C., and 20.4 grams (0.17 mole) of 3-cyanopyridine N-oxide is added portionwise. Upon completion of addition, the reaction mixture is stirred for about 15 minutes, and then 34.4 grams (0.340 mole) of potassium nitrate is added portionwise. Upon completion of addition, the reaction mixture is warmed to about 100° C. where it is stirred for six hours. The reaction mixture is then poured into about 1000 mL of ice-water. The mixture is stirred until the ice melts, and then the resultant solid is collected by filtration. The solid is dried under reduced pressure at about 100° C., yielding 4-nitro-3-cyanopyridine N-oxide.

Step C Synthesis of 2,4-dichloro-3-cyanopyridine as an intermediate

A stirred solution of 19.8 grams (0.12 mole) of 4-nitro-3-cyanopyridine N-oxide in 125 mL of phosphorous oxychloride is heated at reflux for about four hours. The reaction mixture is then poured into about 1500 mL of icewater. The mixture is stirred until the ice melts, then the resultant solid is collected by filtration. The solid is dried under reduced pressure, yielding 2,4-dichloro-3-cyanopyridine.

Step D Synthesis of 2,4-diamino-5-chloro-5-deazapteridine as an intermediate

Under a nitrogen atmosphere, a stirred solution of 17.3 grams (0.10 mole) of 2,4-dichloro-3-cyanopyridine and 36.0 grams (0.20 mole) of guanidine carbonate in 300 mL of N,N-dimethylformamide is heated at reflux for about four hours. After this time the reaction mixture is concentrated under reduced pressure to a residue. The residue is stirred with about 1000 mL of water, and the resultant solid is collected by filtration. The solid is washed with 50 mL of water and dried under reduced pressure, yielding 2,4-diamino-5-chloro-5-deazapteridine.

Step E Synthesis of 2,4-diamino-6-bromo-5-chloro-5-deazapteridine as an intermediate This compound is prepared in a manner analogous to that of Step C of Example 4, using 12.3 grams (0.063 mole) of 2,4-diamino-5-chloro-5-deazapteridine and 11.2 grams (0.063 mole) of N-bromosuccinimide in 250 mL of N,N-dimethylformamide, yielding 2,4-diamino-6-bromo-5-chloro-5-deazapteridine.

Step F Synthesis of 2,4-diamino-5-chloro-6-[3,5-di(trifluoromethyl)-phenyl]-5-deazapteridine (Compound 25)

This compound is prepared in a manner analogous to that of Step D of Example 4, using 2.2 grams (0.008 mole) of 2,4-diamino-6-bromo-5-chloro-5-deazapteridine, 3.2 grams (0.012 mole) of 3,5-di(trifluoromethyl)phenylboronic acid (commercially available), 4.3 grams (0.031 mole) of potassium carbonate and 0.3 gram (catalyst) of tetrakis(triphenylphosphine)palladium(0) in 150 mL of N,N-di-methylformamide, yielding 2,4-diamino-5-chloro- 6-[3,5-di(trifluoromethyl)phenyl]-5-deazapteridine.

Example 14

Synthesis of 2,4-diamino-6-phenyl-5-deazapteridine (COMPOUND 2)

Step A Synthesis of 3-dimethylamino-2-phenylpropenaldehyde as an intermediate

Phosphorus oxychloride, 690 grams (4.5 moles), is warmed to about 30° C., and 478 mL of N,N-dimethylformamide is added dropwise during a two hour period. Upon completion of addition, a solution of 202 grams (1.5 moles) of phenylacetic acid in 158 mL of N,N-dimethylformamide is added dropwise during a one hour period. Upon completion of the addition, the reaction mixture is slowly warmed to about 70°–75° C. where it is stirred for about 16 hours. After this time the reaction mixture is poured into five kilograms of ice. Two kilograms of potassium carbonate are added, and the mixture is stirred until the ice melted. The mixture is separated into two five liter reaction vessels, and 500 mL of toluene is added to each of the vessels. The stirred mixtures are then warmed to about 70° C. where they stirred for about 16 hours. After this time, the mixtures in each vessel are extracted with three 500 mL portions of toluene. The combined extracts are then washed with two one liter portions of water and one one liter portion of an aqueous solution saturated with sodium chloride. The organic layer is dried with potassium carbonate and filtered. The filtrate is concentrated under reduced pressure, yielding 94.9 grams of crude product. The crude product is distilled under vacuum, yielding 78.3 grams of 3-dimethylamino-2-phenylpropenaldehyde, bp 154°–160° C./1 mm Hg. The NMR spectrum is consistent with the proposed structure.

note: The method of M. Julia, et al (Bull. Soc. Chem. France, 7, 1966, 2387–2394) may be used to prepare 3-dimethylamino-2-phenylpropenaldehyde, as described above.

Step B Synthesis of 3-cyano-5-phenylpyridin-2-one as an intermediate

A solution of 52.4 grams (0.97 mole) of sodium methoxide in 600 mL of methanol is stirred, and 37.0 grams (0.44 mole) of 2-cyanoacetamide is added. Immediately upon completion of addition, a solution of 77.9 grams (0.44 mole) of 3-dimethylamino-2-phenylpropenaldehyde in 50 mL of methanol is then added. The reaction mixture is then heated at reflux for about 4.5 hours. After this time the reaction mixture is allowed to cool to ambient temperature as it is stirred during a 72 hour period. The mixture is then cooled at 0° C. for two hours, then filtered to collect a solid. The filtrate is concentrated under reduced pressure to a residue. The residue is slurried with 200 mL of 1:1 acetone/methanol. The acetone/methanol wash is decanted from the solid residue, and the wash procedure using 1:1 acetone/methanol is repeated two additional times. The two solids collected above are combined and slurried in 800 mL of water. The mixture is made acidic (pH 4) with aqueous 10% hydrochloric acid. The resultant mixture is cooled in a refrigerator for about 16 hours, and filtered to collecte a solid. The solid is washed with cold water and cold diethyl ether, yielding when dried, 58.3 grams of 3-cyano-5-phenylpyridin-2-one. The product is taken to the next step without further identification.

Step C Synthesis of 2-chloro-3-cyano-5-phenylpyridine as an intermediate

Under a nitrogen atmosphere, 68.4 grams (0.45 mole) of phosphorus oxychloride is warmed to a gentle reflux, and 38.9 grams (0.18 mole) of 3-cyano- 5-phenylpyridin-2-one is added. Upon completion of addition, 93.6 grams (0.45 mole) of phosphorous pentachloride is added in small portions to maintain the gentle reflux. Upon completion of addition, the reaction mixture is then warmed slowly to about 140° C. where it is stirred for one hour. The reaction mixture is cooled, and excess phosphorus oxychloride is removed under reduced pressure. The concentrate is then poured into 400 grams of ice, where it is stirred until the ice melts. The mixture is then extracted with three 200 mL portions of methylene chloride and 100 mL of diethyl ether. The combined extracts are washed with 150 mL of water and 150 mL of an aqueous solution saturated with sodium chloride. The organic layer is dried with sodium sulfate and filtered. The filtrate is concentrated under reduced pressure at 30° C. to a residue. The residue is distilled under vacuum, yielding 35.4 grams of 2-chloro-3-cyano-5-phenylpyridine, bp 175°–179° C./4 mm Hg., as a crystalline material. The crystalline 2-chloro-3-cyano-5-phenylpyridine is recrystallized from hexane/methylene chloride, mp 149°–150° C.

Step D Synthesis of 2,4-diamino-6-phenyl-5-deazapteridine (Compound 2)

Under a nitrogen atmosphere, a stirred mixture of 0.9 gram (0.005 mole) of guanidine carbonate and 0.5 gram (0.002 mole) of 2-chloro-3-cyano-5-phenylpyridine in 10 mL of dimethylacetamide is heated at 140 ° C. for one hour. After this time the reaction mixture is cooled and filtered to collect a solid. The solid is washed thoroughly with water and dried at 100 ° C., yielding 0.5 gram of 2,4-diamino-6-phenyl-5-deazapteridine, mp 383°–385° C. The NMR spectrum is consistent with the proposed structure.

Note: The method of J. B. Hynes, et al (J.Heterocyclic Chem,25, 1988,1173–1177) may be used to prepare 2,4-diamino-6-phenyl-5-deazapteridine, as described above.

Example 15

Synthesis of 2,4-di(dimethylaminomethyleneamino)-5-methyl-6-[3,5-di(trifluoromethyl)phenyl]-5-deazapteridine (COMPOUND 160)

Under a nitrogen atmosphere, a solution of 1.0 gram (0.0026 mole) of 2,4-diamino-5-methyl-6-[3,5-di(trifluoromethyl)phenyl]-5-deazapteridine (Compound 45-prepared as in Example 4) in 20 mL of dimethylformamide dimethyl acetal is heated at reflux for about 18 hours. After this time, the reaction mixture is cooled and concentrated under reduced pressure to a residue. The residue is then triturated with petroleum ether, and the resulting solid is collected by filtration. The filter cake is washed with petroleum ether and dried, yielding 2,4-di(dimethylaminomethyleneamino)-5-methyl- 6-[3,5-di(trifluoromethyl)phenyl]-5-deazapteridine.

Example 16

Synthesis of 2,4-diamino-5-methyl-6-(4-chlorophenoxy)-5-deazapteridine (COMPOUND 96)

Step A Synthesis of 2-amino-3-cyano-4-methyl-5-(4-chlorophenoxy) pyridine as an intermediate Sodium hydride (60% in mineral oil), 0.4 gram (0.011 mole), is washed with petroleum ether. The petroleum ether is decanted from the sodium hydride, and the sodium hydride is suspended in about 10 mL of N,N-dimethylformamide. The suspension is then stirred, and a solution of 1.3 grams (0.010 mole) of 4-chlorophenol in 10 mL of N,N-dimethylformamide is added. The mixture is stirred for about 10 minutes, then 1.5 grams (0.008 mole) of copper(I) iodide is added. Upon completion of addition, a solution of 2.1 grams (0.008 mole) of 2-amino-3-cyano-4-methyl- 5-iodopyridine in 10 mL of N,N-dimethylformamide is added dropwise. Upon completion of addition, the reaction mixture is stirred at ambient temperature for about 18 hours. The reaction mixture is then cooled and poured into a solution of about 170 mL of water and 20 mL of aqueous 2N sodium hydroxide. The mixture is filtered to collect 2-amino-3-cyano- 4-methyl-5-(4-chlorophenoxy)pyridine.

Step B Synthesis of 2,4-diamino-5-methyl-6-(4-chlorophenoxy)-5-deazapteridine (Compound 96)

This compound is prepared in a manner analogous to that of Step E of Example 4, using 1.2 grams (0.005 mole) of 2-amino-3-cyano-4-methyl-5-(4-chlorophenoxy) pyridine and 0.6 gram (0.010 mole) of guanidine (prepared from 1.0 gram (0.010 mole) of guanidine hydrochloride and 0.5 gram (0.011 mole) of metallic sodium in about 20 mL of anhydrous methanol, filtered to remove sodium chloride), yielding 2,4-diamino-5-methyl- 6-(4-chlorophenoxy)-5-deazapteridine.

Example 17

Synthesis of 2,4-diamino-5-methyl-6-(5-chloro-2,2-dimethylbenzodioxole-7-yl)- 5-deazapteridine (COMPOUND 112)

Step A Synthesis of 3-bromo-5-catechol as an intermediate

A stirring solution of 23.5 grams (0.10 mole) of 2-bromo-4-chloro-6-formylphenol in 100 mL (0.10 mole) of aqueous 1N sodium hydroxide is warmed to about 40° C., and 142 mL (0.13 mole) of aqueous 3% hydrogen peroxide is added. Upon completion of addition, the reaction mixture is stirred at 40° C. for about 18 hours. After this time, the reaction mixture is cooled and made acidic with aqueous 6N hydrochloric acid. The mixture is then concentrated under reduced pressure to a residue. The residue is extracted with four 50 mL portions of hot water. The combined extracts are cooled, and the resulting solid is collected by filtration, yielding about 10 grams of 3-bromo-5-catechol. The NMR spectrum is consistent with the proposed structure.

Step B Synthesis of 7-bromo-5-chloro-2,2-dimethylbenzodixole as an intermediate

A solution of 4.7 grams (0.021 mole) of 3-bromo-5-catechol, and 10 ml (0.136 mole) of acetone in 100 mL of methylene chloride is stirred, and 18.0 grams (0.128 mole) of phosphorus pentoxide is added in one portion. Upon completion of addition, the reaction mixture is stirred at ambient temperature for about 18 hours. After this time, the supernatent liquid is decanted from a solid residue. The residue is washed with methylene chloride, and the wash is combined with the supernatent liquid. The combination is then washed twice each with aqueous 1N sodium hydroxide and an aqueous solution saturated with sodium chloride. The organic layer is then dried with magnesium sulfate and filtered. The filtrate is concentrated under reduced pressure to a residue. The residue is subjected to column chromatography on silica gel, using 5% ethyl acetate in pentane as the eluant. The product-containing fractions are combined and concentrated under reduced pressure, yielding about 0.9 gram of 7-bromo-5-chloro-2, 2-dimethylbenzodioxole. The NMR spectrum is consistent with the proposed structure. This reaction is repeated.

Step C Synthesis of 5-chloro-2,2-dimethylbenzodioxolan-7-ylboronic acid as an intermediate This compound is prepared in a manner analogous to that of Step A of Example 5, using 5.8 grams (0.022 mole) of 7-bromo-5-chloro-2,2-dimethylbenzodioxole, 0.5 gram (0.022 mole) of magnesium turnings, and 3.4 grams (0.033 mole) of trimethyl borate in 100 mL of tetrahydrofuran. The yield of 5-chloro-2,2-dimethylbenzodioxolan-7-ylboronic acid is about 4 grams. The NMR spectrum is consistent with the proposed structure.

Step D Synthesis of 2-amino-3-cyano-4-methyl-5-(5-chloro-2,2-dimethylbenzodioxolan- 7-yl)pyridine as an intermediate This compound is prepared in a manner analogous to that of Step D of Example 4, using 1.7 grams (0.008 mole) of 2-amino-5-bromo-3-cyano-4-methylpyridine, 2.7 grams (0.012 mole) of 5-chloro-2,2-dimethylbenzodioxolan-7-ylboronic acid, 4.3 grams (0.031 mole) of potassium carbonate and 0.3 gram of tetrakis(triphenylphosphine)palladium(0) in 150 mL of toluene, yielding 2-amino-3-cyano-4-methyl-5-(5-chloro-2, 2-dimethylbenzodioxolan-7-yl)pyridine.

Step E Synthesis of 2,4-diamino-5-methyl-6-(5-chloro-2,2-dimethylbenzodioxolan- 7-yl)-5-deazapteridine (Compound 112)

This compound is prepared in a manner analogous to that of Step E of Example 4, using 1.6 grams (0.005 mole) of 2-amino-3-cyano-4-methyl-5-(5-chloro-2,2-dimethylbenzodixole-7-yl)pyridine and 0.6 gram (0.010 mole) of guanidine (prepared from 1.0 gram (0.010 mole) of guanidine hydrochloride and 0.5 gram (0.011 mole) of metallic sodium in about 20 mL of anhydrous methanol, filtered to remove sodium chloride), yielding 2,4-diamino- 5-methyl-6-(5-chloro-2,2-dimethylbenzodioxolan-7-yl)-5deazapteridine.

Example 18

Synthesis of 2,4-di(phenylmethylamino)-5-methyl-6-[3,5-di(trifluoromethyl) phenyl]-5-deazapteridine (COMPOUND 128)

A stirring mixture of 2.0 grams (0.005 mole) of 2,4-diamino-5-methyl-6-[3,5-di(trifluoromethyl)phenyl]-5-deazapteridine (Compound 45-prepared as in Example 4) and 1.2 grams (0.011 mole) of benzaldehyde in 200 mL of ethanol is heated at reflux for about three hours. After this time, the reaction mixture is cooled to ambient temperature and 0.4 gram (0.010 mole) of sodium borohydride is added portion-wise. Upon completion of addition, the reaction mixture is stirred at ambient temperature for about 18 hours. The reaction mixture is then poured into water, and the resultant solid precipitate is collected by filtration. The solid is dried and subjected to column chromatography on silica gel, yielding 2,4-di(phenylmethylamino)-5-methyl-6-[3,5-di(trifluoromethyl)phenyl]-5-deazapteridine.

Example 19

Synthesis of 2,4-diamino-6-bromo-5,7-dimethyl-5-deazapteridine (COMPOUND 196)

Step A Synthesis of 5-bromo-3-cyano-2-hydroxy-4,6-dimethylpyridine as an intermediate Under a nitrogen atmosphere, a stirred solution of 14.9 grams (0.10 mole) of 3-cyano-2-hydroxy-4,6-dimethylpyridine is cooled in an ice bath, and a solution of 18.1 grams (0.10 mole) of N-bromosuccinimide in 50 mL of N,N-dimethylformamide is added dropwise during a 15 minute period. Upon completion of addition, the reaction mixture is stirred at ambient temperature for about 72 hours. After this time, the reaction mixture is diluted to 1000 mL with water and filtered to collect a solid. The solid is dried under vacuum at about 60° C., yielding 22.2 grams of 5-bromo-3-cyano- 2-hydroxy-4,6-dimethylpyridine, mp 254°–262° C. The NMR spectrum is consistent with the proposed structure.

Step B Synthesis of 5-bromo-2-chloro-3-cyano-4,6-dimethylpyridine as an intermediate A mixture of 9.0 grams (0.040 mole) of 5-bromo-3-cyano-2-hydroxy-4,6-dimethylpyridine in 40 mL of phosphorus oxychloride is stirred, and one drop (catalyst) of N,N-dimethylformamide is added. The reaction mixture is then stirred at ambient temperature for about five hours, and then allowed to stand for about 72 hours. After this time, the reaction mixture is poured into 1000 mL of ice containing about one mL of concentrated hydrochloric acid. The mixture is stirred until the ice melts. The resultant precipitate is collected by filtration and washed with water. The solid is then dried under reduced pressure at about 60° C. An NMR spectrum of the solid indicates that it contains a large amount of starting material. The solid is then dissolved in 25 mL of phosphorus oxychloride, and two drops of N,N-dimethylformamide are added. The mixture is heated to reflux where it is stirred for about 18 hours. After this time, the reaction mixture is poured into 600 mL of ice containing about two mL of concentrated hydrochloric acid. The mixture is stirred until the ice melts. The resultant precipitate is collected by filtration, washed with water, and dried under reduced pressure at about 60 ° C., yielding 8.6 grams of 5-bromo-2-chloro-3-cyano-4,6-dimethylpyridine. The NMR spectrum is consistent with the proposed structure.

Step C Synthesis of 2,4-diamino-6-bromo-5,7-dimethyl-5-deazapteridine (Compound 196)

This compound is prepared in a manner analogous to that of Step D of Example 14, using 2.5 grams (0.010 mole) of 5-bromo-2-chloro-3-cyano-4,6-dimethylpyridine and 3.9 grams (0.022 mole) of guanidine carbonate in 30 mL of dimethylacetamide. The yield of 2,4-diamino-6-bromo-5,7-dimethyl- 5-deazapteridine is 2.6 grams. The NMR spectrum is consistent with the proposed structure.

TABLE 1

Substituted 2,4-Diamino-5-deazapteridines as Insecticides

[Structure: 2,4-diamino-5-deazapteridine core with positions labeled: N1, C2 (R²R¹N), N3, C4 (NR³R⁴), C5 (U), C6 (V), C7 (W)]

Where $R^1$, $R^2$, $R^3$, $R^4$, and W are hydrogen;

| Cmpd. No. | U | V |
|---|---|---|
| 1 | H | —$CF_3$ |
| 2 | H | phenyl |
| 3 | H | 2-chlorophenyl |
| 4 | H | 2-($CF_3$)phenyl |
| 5 | H | 3,5-bis($CF_3$)phenyl |
| 6 | H | 2-($OCH_3$)phenyl |
| 7 | H | —$CH_2$-phenyl |
| 8 | H | —$H_2C$-(2,4-difluorophenyl) |
| 9 | H | —$H_2C$-(4-$CF_3$-phenyl) |
| 10 | H | —$H_2C$-(3,5-bis($CF_3$)phenyl) |
| 11 | H | —$(CH_2)_2$-phenyl |
| 12 | H | —S-(3,4-dichlorophenyl) |
| 13 | H | —S(O)-(3,4-dichlorophenyl) |
| 14 | H | —$S(O)_2$-(3,4-dichlorophenyl) |
| 15 | H | —S-(2-naphthyl) |
| 16 | H | —S(O)-(2-naphthyl) |
| 17 | H | —$S(O)_2$-(2-naphthyl) |
| 18 | H | Footnote 1 |
| 19 | Cl | phenyl |
| 20 | Cl | 4-chlorophenyl |
| 21 | Cl | 4-fluorophenyl |
| 22 | Cl | 2,4-dichlorophenyl |
| 23 | Cl | 3,5-dichlorophenyl |
| 24 | Cl | 2-chloro-4-fluorophenyl |

TABLE 1-continued

Substituted 2,4-Diamino-5-deazapteridines as Insecticides

| # | $R^1R^2N$ / $R^3R^4N$ | substituent |
|---|---|---|
| 25 | Cl | 3,5-bis(CF$_3$)phenyl |
| 26 | Cl | 1-naphthyl |
| 27 | F | 4-(CO$_2$CH$_3$)phenyl-CH$_2$-N(H)(CH$_3$)- (methyl 4-((methylamino)methyl)benzoate) |
| 28 | —CH$_3$ | phenyl |
| 29 | —CH$_3$ | 3-chlorophenyl |
| 30 | —CH$_3$ | 4-chlorophenyl |
| 31 | —CH$_3$ | 3-fluorophenyl |
| 32 | —CH$_3$ | 3,5-dichlorophenyl |
| 33 | —CH$_3$ | 3,5-difluorophenyl |
| 34 | —CH(CH$_3$)$_2$ | 3,5-difluorophenyl |
| 35 | —CH$_3$ | 2-chloro-4-fluorophenyl |
| 36 | —CH$_3$ | 2-methylphenyl |
| 37 | —CH$_3$ | 3-methylphenyl |
| 38 | —CH$_3$ | 4-methylphenyl |
| 39 | —CH$_3$ | 2-methoxy-4-chlorophenyl |
| 40 | —CH$_3$ | 3,5-dimethylphenyl |
| 41 | —CH$_3$ | 2-(CF$_3$)phenyl |
| 42 | —CH$_3$ | 3-(CF$_3$)phenyl |
| 43 | —CH$_3$ | 4-(CF$_3$)phenyl |
| 44 | —CH$_3$ | 3-fluoro-5-(CF$_3$)phenyl |
| 45 | —CH$_3$ | 3,5-bis(CF$_3$)phenyl |
| 46 | —CH$_3$ HCl Salt | 3,5-bis(CF$_3$)phenyl |

TABLE 1-continued

Substituted 2,4-Diamino-5-deazapteridines as Insecticides

[Structure: 2,4-diamino-5-deazapteridine core with NR³R⁴ at position 4, U at position 5, V at position 6, W at position 7, R²R¹N at position 2]

| Cmpd. No. | R¹ / Salt | V |
|---|---|---|
| 47 | —CH₃, Ethanesulfonic Acid Salt | 3,5-bis(CF₃)phenyl |
| 48 | —CH₃, Gluconic Acid Salt | 3,5-bis(CF₃)phenyl |
| 49 | —CH₃, Pamoic Acid Salt | 3,5-bis(CF₃)phenyl |
| 50 | —CH(CH₃)₂ | 3,5-bis(CF₃)phenyl |
| 51 | —CH₃ | 3-CF₃-5-CO₂CH₃-phenyl |
| 52 | —CH₃ | 3-OC₃H₇-phenyl |
| 53 | —CH₃ | 3-CH₂OCH₃-phenyl |
| 54 | —CH₃ | 3-OCF₃-phenyl |
| 55 | —CH₃ | 3-CN-phenyl |
| 56 | —CH₃ | 3-SCH₂CH₃-phenyl |
| 57 | —CH₃ | 3-SO₂C₂H₅-phenyl |
| 58 | —CH₃ | 3-SC₄H₉-phenyl |
| 59 | —CH₃ | 3-SO₂C₄H₉-phenyl |

Where R¹, R², R³, R⁴, and W are hydrogen; U is methyl; and V is:

[Structure: phenyl with R⁵ at ortho, X at para, Y at meta positions]

| Cmpd. No. | X | Y | R⁵ |
|---|---|---|---|
| 60 | H | H | phenyl |
| 61 | H | H | 4-Cl-phenyl |
| 62 | F | H | 4-F-phenyl |
| 63 | F | F | phenyl |
| 64 | H | H | 4-CF₃-phenyl |

Where R¹, R², R³, R⁴, and W are hydrogen; U is methyl; and V is:

[Structure: phenyl with X, R⁵, Y substituents]

| Cmpd. No. | X | Y | R⁵ |
|---|---|---|---|
| 65 | H | H | phenyl |
| 66 | H | H | 4-Cl-phenyl |
| 67 | H | H | 4-CF₃-phenyl |

TABLE 1-continued

Substituted 2,4-Diamino-5-deazapteridines as Insecticides

[Structure: 2,4-diamino-5-deazapteridine core with positions labeled NR³R⁴ at 4, U at 5, V at 6, W at 7, R²R¹N at 2, and N at 1, 3]

| Cmpd. No. | | | |
|---|---|---|---|
| 68 | H | Cl | 4-fluorophenyl |
| 69 | H | F | 4-fluorophenyl |
| 70 | —CH₃ | H | phenyl |

Where R¹, R², R³, R⁴, and W are hydrogen; and V is:

[Structure: phenyl ring with OR⁶ (ortho) and X (para) substituents]

| Cmpd. No. | U | X | R⁶ |
|---|---|---|---|
| 71 | Cl | Cl | —CH₃ |
| 72 | Cl | Cl | —CH₂-(4-chlorophenyl) |
| 73 | Cl | Cl | —(CH₂)₄-(4-chlorophenyl) |
| 74 | —CH₃ | H | 4-chlorophenyl |
| 75 | —CH₃ | H | 4-fluorophenyl |
| 76 | —CH₃ | Cl | 4-fluorophenyl |
| 77 | —CH₃ | F | 4-chlorophenyl |
| 78 | —CH₃ | —CF₃ | 4-chlorophenyl |
| 79 | —CH₃ | —OCF₃ | 4-fluorophenyl |

Where R¹, R², R³, R⁴, and W are hydrogen, and V is:

[Structure: phenyl ring with OR⁶ and X substituents in 1,3,5 positions]

| Cmpd. No. | U | X | R⁶ |
|---|---|---|---|
| 80 | —CH₃ | H | phenyl |
| 81 | —CH₃ | Cl | 4-chlorophenyl |
| 82 | —CH₃ | F | 4-fluorophenyl |
| 83 | —CH₃ | —CF₃ | 4-chlorophenyl |
| 84 | —CH₃ | —OCF₃ | 4-fluorophenyl |
| 85 | —CH₃ | —CH₃ | 4-fluorophenyl |

Where R¹, R², R³, R⁴, and W are hydrogen, and U is methyl.

| Cmpd. No. | V |
|---|---|
| 86 | —H₂C-(2,4-difluorophenyl) |
| 87 | —H₂C-(2,4-dichloro-5-bromophenyl) |
| 88 | —H₂C-(4-trifluoromethylphenyl) |

TABLE 1-continued

Substituted 2,4-Diamino-5-deazapteridines as Insecticides $$\begin{array}{c} NR^3R^4 \quad U \\ \underset{R^2R^1N}{\overset{N}{\underset{}{\bigvee}}} \underset{N}{\overset{}{\bigvee}} \underset{W}{\overset{V}{\bigvee}} \end{array}$$

| Cmpd. No. | Structure |
|---|---|
| 89 | —H$_2$C—(3,5-bis(CF$_3$)phenyl) |
| 90 | —H$_2$C—(2,5-dimethoxyphenyl) |
| 91 | —CH$_2$CH$_2$—phenyl |
| 92 | —CH$_2$CH$_2$—(3-CF$_3$ phenyl) |
| 93 | —CH$_2$CH$_2$—(3,5-bis(CF$_3$)phenyl) |
| 94 | —O—(2-Cl phenyl) |
| 95 | —O—(3-Cl phenyl) |
| 96 | —O—(4-Cl phenyl) |
| 97 | —O—(2,5-diCl phenyl) |
| 98 | —O—(2-CF$_3$ phenyl) |
| 99 | —O—(3-CF$_3$ phenyl) |
| 100 | —O—(3,5-bis(CF$_3$)phenyl) |
| 101 | 2-thienyl |

Where R$^1$, R$^2$, R$^3$, R$^4$, and W are hydrogen, U is methyl; and V is:

benzofuran-like bicyclic with substituents A, B, D and gem-dimethyl at 2-position

| Cmpd. No. | A | B | D |
|---|---|---|---|
| 102 | O | —CH$_2$— | H |
| 103 | —CH$_2$— | O | H |
| 104 | O | —CH$_2$— | Cl |
| 105 | —CH$_2$— | O | Cl |
| 106 | O | C=O | H |
| 107 | C=O | O | Cl |
| 108 | O | —CH$_2$— | F |
| 109 | O | —CH$_2$— | —CH$_3$ |
| 110 | O | —CH$_2$— | —CF$_3$ |
| 111 | O | O | H |
| 112 | O | O | Cl |
| 113 | O | O | F |
| 114 | O | O | —CH$_3$ |
| 115 | O | O | —CF$_3$ |

Where R$^1$, R$^2$, R$^3$, R$^4$, and W are hydrogen;

| Cmpd. No. | U | V |
|---|---|---|
| 116 | Br | H |
| 117 | I | H |
| 118 | —OC$_2$H$_5$ | H |
| 119 | —OCH$_2$CF$_3$ | H |
| 120 | —CF$_3$ | H |
| 121 | —N(CH$_3$)$_2$ | H |
| 122 | —CN | H |
| 123 | phenyl | H |
| 124 | —S—(3,4-diCl phenyl) | H |
| 125 | —S(O)—(3,4-diCl phenyl) | H |
| 126 | —SCH$_2$—(3,4-diCl phenyl) | H |

TABLE 1-continued

Substituted 2,4-Diamino-5-deazapteridines as Insecticides

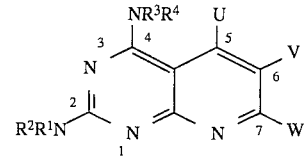

| Cmpd. No. | V |
|---|---|
| 127 | —(CH$_2$)$_2$-[2-naphthyl] H |

Where R$^1$, R$^3$, and W are hydrogen, U is methyl; and R$^2$ and R$^4$ are:

[phenethyl group]

| Cmpd. No. | V |
|---|---|
| 128 | 3,5-bis(CF$_3$)phenyl |
| 129 | 3,5-dichloro-4-methoxyphenyl |

Where R$^1$, R$^3$, and W are hydrogen, U is methyl,
V is 3,5-bis(CF$_3$)phenyl  R$^2$ and R$^4$ are
$-C(=O)R^7$ ;

| Cmpd. No. | R$^7$ |
|---|---|
| 130 | —CH$_3$ |
| 131 | —C$_5$H$_{11}$ |
| 132 | —C$_8$H$_{17}$ |
| 133 | —CH(CH$_3$)$_2$ |
| 134 | —C(CH$_3$)$_3$ |
| 135 | —C$_2$F$_5$ |
| 136 | n-OC$_4$H$_9$ |
| 137 | —OC(CH$_3$)$_3$ |
| 138 | —OC$_2$H$_4$OC$_2$H$_4$OCH$_3$ |
| 139 | —C≡CCH$_3$ |
| 140 | —CH$_2$SO$_2$CH$_3$ |
| 141 | —CH$_2$OC$_2$H$_5$ |
| 142 | —C$_2$H$_4$OC$_2$H$_5$ |
| 143 | —CH$_2$OC$_2$H$_4$OC$_2$H$_5$ |
| 144 | —CH$_2$OC$_2$H$_4$OC$_2$H$_5$ |
| 145 | —C$_2$H$_4$OC$_2$H$_4$OC$_2$H$_5$ |
| 146 | —CH$_2$OC$_2$H$_4$OC$_2$H$_4$OCH$_3$ |

Where R$^1$, R$^3$, and W are hydrogen, U is methyl,

TABLE 1-continued

Substituted 2,4-Diamino-5-deazapteridines as Insecticides

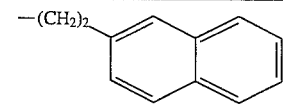

V is 3,5-dichlorophenyl   R$^2$ and R$^4$ are $-C(=O)R^7$ ;

| Cmpd. No. | R$^7$ |
|---|---|
| 147 | —CH$_3$ |
| 148 | —C$_5$H$_{11}$ |
| 149 | —C$_8$H$_{17}$ |
| 150 | —C$_{11}$H$_{23}$ |
| 151 | —CH(CH$_3$)$_2$ |
| 152 | —C(CH$_3$)$_3$ |
| 153 | —CH$_2$CF$_3$ |
| 154 | —C$_2$F$_5$ |
| 155 | —C$_5$F$_{11}$ |
| 156 | —CH$_2$C≡N |
| 157 | phenyl |
| 158 | 4-chlorophenyl |
| 159 | 3-pyridyl |

Where W is hydrogen, U is methyl,
V is 3,5-bis(CF$_3$)phenyl

R$^1$ and R$^2$ taken together, and R$^3$ and R$^4$ taken together each form the group

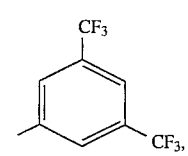

| Cmpd No | R$^9$ | R$^{10}$ |
|---|---|---|
| 160 | —CH$_3$ | —CH$_3$ |
| 161 | —CH(CH$_3$)$_2$ | —CH(CH$_3$)$_2$ |
| 162 | —CH$_2$CH$_2$CH$_2$CH$_2$CH$_2$— | |

Where R$^1$, R$^2$, R$^3$, R$^4$, and W are hydrogen; U is methyl; and V is:

| Cmpd. No | U$^1$ | V$^1$ | W$^1$ | X$^1$ | Y$^1$ | Z$^1$ |

TABLE 1-continued

Substituted 2,4-Diamino-5-deazapteridines as Insecticides (Structure: 2,4-diamino-5-deazapteridine core with positions labeled — $NR^3R^4$ at 4, U at 5, V at 6, W at 7, $R^2R^1N$ at 2)

| Cmpd | | | | | | |
|---|---|---|---|---|---|---|
| 163 | Cl | H | H | H | H | H |
| 164 | Cl | H | $-CF_3$ | H | H | H |
| 165 | Cl | H | H | $-CF_3$ | H | H |
| 166 | H cis | H | H | Cl | H | H |
| 167 | H trans | H | H | Cl | H | H |
| 168 | H cis | H | H | F | H | H |
| 169 | H trans | H | H | F | H | H |
| 170 | H cis | H | H | $-CF_3$ | H | H |
| 171 | H trans | H | H | $-CF_3$ | H | H |

Where $R^1$, $R^2$, $R^3$, $R^4$, and W are hydrogen; U is methyl; and V is:

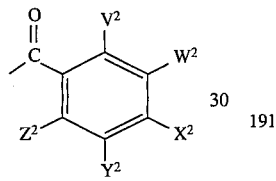

| Cmpd. No. | $V^2$ | $W^2$ | $X^2$ | $Y^2$ | $Z^2$ |
|---|---|---|---|---|---|
| 172 | H | H | H | H | H |
| 173 | Cl | H | H | H | H |
| 174 | H | Cl | H | H | H |
| 175 | H | H | Cl | H | H |
| 176 | $-CF_3$ | H | H | H | H |
| 177 | H | $-CF_3$ | H | H | H |
| 178 | H | H | $-CF_3$ | H | H |
| 179 | H | $-CO_2CH_3$ | H | H | H |
| 180 | H | H | $-CO_2CH_3$ | H | H |
| 181 | H | F | H | F | H |
| 182 | H | H | F | H | H |
| 183 | F | H | F | H | F |
| 184 | H | 4-F-phenyl | H | H | H |
| 185 | H | 4-Cl-phenyl | H | H | H |
| 186 | H | H | 4-F-phenyl | H | H |
| 187 | H | H | 4-Cl-phenyl | H | H |

Where $R^1$, $R^2$, $R^3$, $R^4$, and W are hydrogen; and V is:

TABLE 1-continued

Substituted 2,4-Diamino-5-deazapteridines as Insecticides (Same core structure as above)

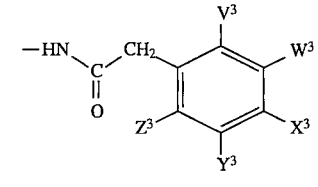

| Cmpd. No. | U | $V^3$ | $W^3$ | $X^3$ | $Y^3$ | $Z^3$ |
|---|---|---|---|---|---|---|
| 188 | | H | H | H | Cl | Cl | H |
| 189 | | Cl | H | H | Cl | Cl | H |

Where $R^1$, $R^2$, $R^3$, and $R^4$ are hydrogen;

| Cmpd. No. | U | V | W |
|---|---|---|---|
| 190 | $-CH_3$ | 3,5-difluorophenyl | F |
| 191 | $-CH_3$ | 3,5-bis(CF$_3$)phenyl | F |
| 192 | phenyl | $-H_2C$-phenyl | $-SH$ |
| 193 | $-CH_3$ | 3,5-bis(CF$_3$)phenyl | $-CH_3$ |
| 194 | $-CH_3$ | 3,5-dichlorophenyl | $-CH_3$ |
| 195 | $-CH_3$ | phenyl | $-CH_3$ |
| 196 | $-CH_3$ | Br | $-CH_3$ |
| 197 | $-CH_3$ | I | $-CH_3$ |
| 198 | H | Br | $-CH_3$ |
| 199 | H | I | $-CH_3$ |
| 200 | H | phenyl | $-CH_3$ |
| 201 | H | 3,5-bis(CF$_3$)phenyl | $-CH_3$ |
| 202 | $-C(CH_3)_3$ | Br | H |
| 203 | $-C(CH_3)_3$ | phenyl | H |

TABLE 1-continued

Substituted 2,4-Diamino-5-deazapteridines as Insecticides

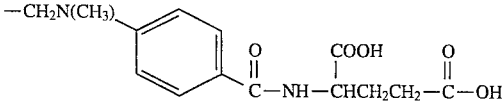

| Cmpd | R | V | W |
|---|---|---|---|
| 204 | —C(CH$_3$)$_3$ | 3,5-bis(CF$_3$)phenyl | H |

FOOTNOTES
[1] In Compound 18, X is
—CH$_2$N(CH$_3$)—C$_6$H$_4$—C(O)—NH—CH(COOH)CH$_2$CH$_2$—C(O)—OH

TABLE 1A

Substituted 2,4-Diamino-7-hydroxy-5-deazapteridine Intermediates

Where R$^1$, R$^2$, R$^3$, and R$^4$ are hydrogen;

| Cmpd. No. | U | V |
|---|---|---|
| 1A | H | 3,5-bis(CF$_3$)phenyl |
| 2A | —CH$_3$ | phenyl |
| 3A | —CH$_3$ | 3,5-bis(CF$_3$)phenyl |
| 4A | —CH$_3$ | —H$_2$C—(2-OCH$_3$, 4-Cl phenyl) |
| 5A | —CH$_3$ | —H$_2$C—phenyl |
| 6A | —CH$_3$ | —H$_2$C—(2,4-Cl, 5-Br phenyl) |
| 7A | —CH$_3$ | —H$_2$C—(3,5-bis(CF$_3$)phenyl) |
| 8A | —CH$_3$ | —H$_2$C—(2,5-di-OCH$_3$ phenyl) |
| 9A | —CH$_3$ | 4-Cl, 6-CH$_3$, 2-OCH$_2$C(CH$_3$)$_3$ phenyl |
| 10A | —CH$_3$ | 2,6-di-CH$_3$, -C(O)C(CH$_3$)$_3$ phenyl |
| 11A | —OC$_2$H$_5$ | H |

Where R$^1$, R$^2$, R$^3$, and R$^4$ are hydrogen; U is methyl; and V is:

3-R$^5$, 4-Y, 5-X phenyl

| Cmpd. No. | X | Y | R$^5$ |
|---|---|---|---|
| 12A | F | H | 4-F-phenyl |

Where R$^1$, R$^2$, R$^3$, and R$^4$ are hydrogen, and V is:

3-OR$^6$, 5-X phenyl

| Cmpd. No. | U | X | R$^6$ |
|---|---|---|---|

TABLE 1A-continued

Substituted 2,4-Diamino-7-hydroxy-5-deazapteridine Intermediates

| 13A | —CH₃ | —CH₃ | 4-Cl-phenyl |
| 14A | —CH₃ | F | 4-F-phenyl |

Where $R^1$, $R^2$, $R^3$, $R^4$, and W are hydrogen; U is methyl; and V is:

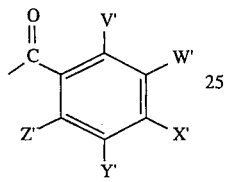

| Cmpd. No. | V' | W' | X' | Y' | Z' |
|---|---|---|---|---|---|
| 15A | H | H | —CF₃ | H | H |

TABLE 1B

Substituted 2,4-Diamino-7-chloro-5-deazapteridine Intermediates

Where $R^1$, $R^2$, $R^3$, and $R^4$ are hydrogen;

| Cmpd. No. | U | V |
|---|---|---|
| 1B | H | 3,5-bis(CF₃)phenyl |
| 2B | —CH₃ | phenyl |
| 3B | —CH₃ | 3,5-bis(CF₃)phenyl |
| 4B | —CH₃ | —H₂C—(2-OCH₃, 5-Cl)phenyl |
| 5B | —CH₃ | —H₂C—phenyl |
| 6B | —CH₃ | —H₂C—(2-Cl, 4-Cl, 5-Br)phenyl |
| 7B | —CH₃ | —CH₂—(3,5-bis(CF₃))phenyl |
| 8B | —CH₃ | —H₂C—(2-OCH₃, 5-OCH₃)phenyl |
| 9B | —CH₃ | (4-Cl-2,6-dimethyl)phenyl-CH₂-C(CH₃)₂-C(=O)— |
| 10B | —CH₃ | (2,6-dimethyl)phenyl-C(=O)-C(CH₃)₂-O— |
| 11B | —OC₂H₅ | H |

Where $R^1$, $R^2$, $R^3$, and $R^4$ are hydrogen; U is methyl; and V is:

2-methyl-4-X, 5-Y, R⁵-phenyl structure

| Cmpd. No. | X | Y | R⁵ |
|---|---|---|---|
| 12B | F | H | 4-F-phenyl |

Where $R^1$, $R^2$, $R^3$, and $R^4$ are hydrogen, and V is:

TABLE 1B-continued

Substituted 2,4-Diamino-7-chloro-5-deazapteridine Intermediates

[Structure: pteridine core with positions labeled 1-7, substituents NR³R⁴ at 4, U at 5, V at 6, Cl at 7, R²R¹N at 2]

[Structure: phenyl ring with OR⁶ and X substituents]

| Cmpd. No. | U | X | R⁶ |
|---|---|---|---|
| 13B | —CH₃ | —CH₃ | [4-chlorophenyl] |
| 14B | —CH₃ | F | [4-fluorophenyl] |

Where R¹, R², R³, R⁴, and W are hydrogen; U is methyl; and V is:

[Structure: C(=O)-phenyl with V', W', X', Y', Z' substituents]

| Cmpd. No. | V' | W' | X' | Y' | Z' |
|---|---|---|---|---|---|
| 15B | H | H | —CF₃ | H | H |

Insecticide Formulations

In the normal use of the insecticidal 5-deazapteridines of the present invention, they usually will not be employed free from admixture or dilution, but ordinarily will be used in a suitable formulated composition compatible with the method of application and comprising an insecticidally effective amount of the pteridines. The 5-deazapteridines of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present pteridines may be applied, for example, as sprays, dusts, or granules to the area where pest control is desired, the type of application varying of course with the pest and the environment. Thus, the 5-deazapteridines of this invention may be formulated as granules of large particle size, as powdery dusts, as wettable powders, as emulsifiable concentrates, as solutions, and the like. It will be understood that the insecticides themselves may be present as essentially pure compounds, or as mixtures of these pteridines compounds.

Granules may comprise porous or nonporous particles, such as attapulgite clay or sand, for example, which serve as carriers for the ptefidines. The granule particles are relatively large, a diameter of about 400–2500 microns typically. The particles are either impregnated with the pteridine from solution or coated with the pteridine, adhesive sometimes being employed. Granules generally contain 0.05–10%, preferably 0.5–5%, active ingredient as the insecticidally effective amount.

Dusts are admixtures of the prteridines with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects contains 1 part of Compound 90 and 99 parts of talc.

The 5-deazapteridines of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% 5-deazapteridine, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts. By way of illustration, Compound 90 is formulated as a 10% wettable powder (10% WP) as follows:

| COMPONENT | AMOUNT (wt/wt) |
|---|---|
| Compound 90 | 10.1% |
| Wetting Agent | 5.0% |
| Dispersing Agent | 3.8% |
| Wetting/Dispersing Agent | 0.9% |
| Diluent | 80.2% |

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the 5-deazapteridines with a liquid or solid emulsifying agent, or they may also contain a liquid carder such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts, including fatty methyl tauridines; alkylaryl polyether alcohols; sulfates of higher alcohols; polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal composition.

Other useful formulations include simple solutions of the active ingredient in a solvent in which it is completely soluble at the desired concentrations, such as acetone or other organic solvents.

As shown in the biological test methods below, the compounds of the present invention are tested in the laboratory as dimethyl sulfoxide solutions incorporated into an artificial insect diet. Alternatively, they could be used as aqueous acetone or methanol solutions containing a small amount of octylphenoxypolyethoxyethanol surfactant for use as foliar sprays. An insecticidally effective amount of pteridine in an insecticidal composition diluted for application is normally in the range of about 0.001% to about 8% by weight. Many variations of spraying and dusting compositions known in the art may be used by substituting the 5-deazapteridine of this invention into compositions known or apparent in the art.

The insecticidal compositions of this invention may be formulated with other active ingredients, including other insecticides, nematicides, acaricides, fungicides, plant growth regulators, fertilizers, etc.

In using the compositions to control insects, it is only necessary that an insecticidally effective amount of 5-deazapteridine be applied to the locus where control is desired. Such locus may, e.g., be the insects themselves, plants upon which the insects feed, or the insect habitat. When the locus is the soil, e.g., soil in which agricultural crops are or will be planted, the active compound may be applied to and optionally incorporated into the soil. For most applications, an insecticidally effective amount will be about 75 to 4000 g per hectare, preferably 150 g to 3000 g per hectare.

Biological Data

The 5-deazapteridines of the present invention were incorporated into an artificial diet for evaluation of insecticidal activity against the tobacco budworm (*Heliothis virescens* [Fabricius]).

Stock solutions of test chemical in dimethyl sulfoxide were prepared for each rate of application. The rates of application, expressed as the negative log of the molar concentration, and the corresponding concentrations of the stock solution prepared for each rate are shown below:

| Stock Solution | Rate of Application |
| --- | --- |
| 50 micromolar | 4 |
| 5 | 5 |
| 0.5 | 6 |
| 0.05 | 7 |
| 0.005 | 8 |

One hundred microliters of each of the stock solutions was manually stirred into 50 mL of a molten (65°–70 °C.) wheat germ-based artificial diet. The 50 mL of molten diet containing the test chemical was poured evenly into twenty wells in the outer four rows of a twenty-five well, five row plastic tray. Each well in the tray was about 1 cm in depth, with an opening of 3 cm by 4 cm at the lip. Molten diet containing only dimethyl sulfoxide at the levels used in the test chemical-treated diet was poured into the five wells in the third row of the tray. Each tray therefore contained one test chemical at a single rate of application, together with an untreated control.

Single second instar tobacco budworm larvae were placed in each well. The larvae were selected at a stage of growth at which they uniformly weigh about 5 mg each. Upon completion of infestation, a sheet of clear plastic was heat-sealed over the top of the tray using a common household flat iron. The trays were held at 25° C. at 60% relative humidity for five days in a growth chamber. Lighting was set at 14 hours of light and 10 hours of darkness.

After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($pI_{50}$) was determined by linear regression, when possible, for each test chemical. Where possible, the negative log of the concentration of the test chemical that provided 50% mortality ($pLC_{50}$) was also determined.

The compounds of the present invention were tested in the diet test as insect growth inhibitors against the larvae of tobacco budworm (above). The results of this testing are set forth in Table 2 below.

TABLE 2

Insecticidal Activity of Substituted 2,4-Diamino-5-Deazapteridines Incorporated Into the Diet of Tobacco Budworm

| Cmpd. No. | Rate of Application[1] | Percent Growth Inhibition[2] | $pI_{50}$[3] | Percent Mortality[4] | $pLC_{50}$[5] |
| --- | --- | --- | --- | --- | --- |
| 90 | 7 | 26 | 6.0 | — | — |
|  | 6 | 41 |  | — |  |
|  | 5 | 87 |  | — |  |
|  | 4 | 95 |  | — |  |

FOOTNOTES
[1]The rate of application is expressed as the negative log of the molar concentration of the test compound in the diet.
[2]Percent growth inhibition is derived from the total weight of the insects (IW) at each rate of application in the test relative to the total weight of insects in an untreated control,
% Gr. Inh. = [IW (control) − IW (test)/IW (control)] × 100
[3]$pI_{50}$ is the negative log of the concentration of the test chemical that provides 50% growth inhibition in the test insects.
[4]Percent mortality is derived from the number of dead insects (TD) relative to the total number of insects (TI) used in the test,
% Mortality = $\frac{TD}{TI}$ × 100
[5]$pLC_{50}$ is the negative log of the concentration of the test chemical that provides 50% mortality of the test insects.

In a further embodiment of this invention, several of the compounds disclosed above have themselves been found to be novel and useful intermediates in the preparation of the 5-deazapteridine insecticides disclosed and claimed herein.

Included among these intermediate compounds are those having the following formula:

$$\text{(II)}$$

[structure: pyridine ring with NC and U at top, V at right, W at bottom right adjacent to N, and $H_2N$ at bottom left]

wherein

W is hydrogen, and lower alkyl (e.g., —CH$_3$,).

U is hydrogen, halogen (e.g., Br, Cl, F, I), lower alkyl [e.g.,—CH$_3$, —CH(CH$_3$)$_2$], lower alkoxy (e.g.,— OC$_2$H$_5$), lower haloalkyl (e.g., —CF$_3$), V is halogen (e.g., Br, I), alkenyl [e.g., 2-(4-chlorophenyl)ethenyl], alkynyl (e.g., ethynyl, trimethylsilylethynyl, 4-chlorophenylethynyl); substituted aryl [e.g., 4-chlorophenyl, 3,5-di(trifluoromethyl)phenyl, 3-fluoro-5-(4-fluorophenyl)phenyl]; substituted aryloxy (e.g., 4-chlorophenoxy), arylcarbonyl (e.g., phenylcarbonyl), or a benzo-fused oxygen containing heterocycle of the formula:

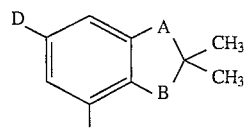

wherein A and B are independently selected from methylene, oxygen, or carbonyl, and; D is hydrogen, halogen (e.g., Cl, Br), lower alkyl (e.g., —CH₃), or lower haloalkyl (e.g., —CF₃);

with the proviso that when V is substituted aryl, U is other than hydrogen.

These novel intermediates, as shown in the above example, may readily be prepared from known starting materials by conventional means. Illustrations of these intermediates of structure II, and their preparation, include 2-amino-5-bromo-3-cyano-4-methylpyridine and 2-amino-3-cyano-4-methyl- 5-[3,5-di(trifluoromethyl)phenyl]pyridine (see Example 4); 2-amino-3-cyano- 4-methyl-5-[3-fluoro-5-(4-fluorophenoxy)phenyl]pyridine (see Example 7); 2-amino-3-cyano-4-methyl-5-(6-chloro-2,3-dihydro-2,2-dimethylbenzofuran-4-yl) pyridine (see Example 8); 2-amino-3-cyano-5-iodo-4-methylpyridine and 2-amino-3-cyano-4-methyl-5-(2,3-dihydro-2,2-dimethyl- 3-benzofuranon-4-yl)pyridine (see Example 9); as well as those of Examples 5, 6, 10, 11, and 18.

Conversion of these intermediates to the insecticides of this invention likewise employs methods well-known to those skilled in the art; and in any event these methods are fully documented by the processes of the above examples.

In each of these methods the nature of the substituents on the final product may readily be determined by selection of the correspondingly substituted starting materials as shown in the examples above, or by introduction of such groups by means well known to those skilled in the art such as conventional halogenation or reduction reactions, or the like, also shown in the above examples.

We claim:

1. Compounds having the formula:

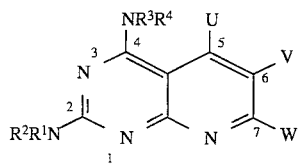

wherein $R^1$ is hydrogen, lower alkyl, or arylalkyl;

$R^3$ is hydrogen, lower alkyl, or arylalkyl;

$R^2$ and $R^4$ are independently hydrogen, lower alkyl, arylalkyl, or

wherein $R^7$ is straight or branched chain alkyl, cycloalkyl, lower haloalkyl, lower alkynyl, straight or branched chain alkoxy, alkylsulfonylalkyl, aryl, arylalkyloxy, or ethers, or polyethers of two to twelve carbon atoms in length containing one to four ether linkages; or $R^1$ and $R^2$ taken together, and $R^3$ and $R^4$ taken together, each form the group —$R^8$—O—$R^8$, wherein $R^8$ is lower alkylene; or form the group

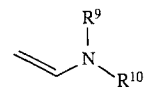

wherein $R^9$ and $R^{10}$ are independently straight or branched chain lower alkyl, or $R^9$ and $R^{10}$ taken together with two to five methylene groups form an alkylene ring;

W is hydrogen, halogen, lower alkyl, or hydroxy;

U is hydrogen, halogen, lower haloalkyl, lower alkoxy, lower haloalkoxy, lower dialkylamino, arylalkyl, substituted arylthio, substituted arylsulfinyl, or substituted arylalkylthio; and V is thienyl, substituted aryl, arylsulfinyl or substituted arylsuifinyl, arylsulfonyl or substituted arylsulfonyl, (aryl)(halo)alkenyl or substituted (aryl)(halo) alkenyl, aroyl or substituted aroyl, or a benzo-fused oxygen-containing heterocycle of the formula:

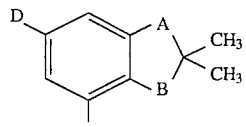

A and B are independently selected from methylene, carbonyl, and oxygen, and wherein at least one of A and B is oxygen;

wherein D is hydrogen, halogen, lower alkyl, or lower haloalkyl; to form, the heterocycle 2,3-dihydro-2, 2-dimethylbenzofuran-4-yl, 2,3-dihydro-2,2-dimethylbenzofuranan- 7-yl, 6-halo-2,3-dihydro-2, 2-dimethylbenzofuran-4-yl, 5-halo-2,3-dihydro-2,2-dimethylbenzofuranan- 7-yl, 2,3-dihydro-2,2-dimethyl-3-benzofuranon-4-yl, or 2,2-dimethyl-5-halobenzodioxole-7-yl.

2. The compound of claim 1 wherein $R^1$, $R^2$, $R^3$, $R^4$ and W are hydrogen;

U is lower alkyl;

and

V is substituted aryl, aroyl or substituted aroyl, (aryl)(halo)alkenyl or substituted (aryl)(halo)alkenyl, or a benzo-fused oxygen-containing heterocycle of the formula:

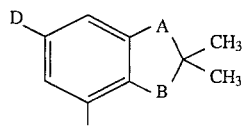

wherein A and B are independently selected from methylene, carbonyl, and oxygen, and wherein at least one of A and B is oxygen, and wherein D is hydrogen, halogen, lower alkyl, or lower haloalkyl; to form, the heterocycle 2,3-dihydro-2, 2-dimethylbenzofuran-4-yl, 2,3-dihydro-2, 2-dimethylbenzofuran-7-yl, 6-halo-2,3-dihydro-2, 2-dimethylbenzofuran-4-yl, 5-halo-2,3-dihydro-2, 2-dimethylbenzofuran-7-yl, 2,3-dihydro-2,2-dimethyl-3-benzofuranon-4-yl, or 2,2-dimethyl-5-halobenzodioxol-7-yl.

* * * * *